(12) United States Patent
Sakamaki et al.

(10) Patent No.: US 10,973,742 B2
(45) Date of Patent: Apr. 13, 2021

(54) PHOTOCURABLE COMPOSITION, DENTURE BASE, AND PLATE DENTURE

(71) Applicant: Mitsui Chemicals, Inc., Tokyo (JP)

(72) Inventors: Toshikazu Sakamaki, Tokyo (JP); Kouya Kojima, Urayasu (JP); Hirohisa Shiode, Yokohama (JP); Mai Kimura, Sodegaura (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 16/322,808

(22) PCT Filed: Aug. 2, 2017

(86) PCT No.: PCT/JP2017/028150
§ 371 (c)(1),
(2) Date: Feb. 1, 2019

(87) PCT Pub. No.: WO2018/025943
PCT Pub. Date: Feb. 8, 2018

(65) Prior Publication Data
US 2019/0175455 A1 Jun. 13, 2019

(30) Foreign Application Priority Data

Aug. 2, 2016 (JP) .............................. JP2016-152160

(51) Int. Cl.
| | | |
|---|---|---|
| C08F 2/46 | (2006.01) | |
| C08F 2/50 | (2006.01) | |
| C08G 61/04 | (2006.01) | |
| A61K 6/887 | (2020.01) | |
| A61K 6/00 | (2020.01) | |
| A61K 6/62 | (2020.01) | |
| A61C 13/01 | (2006.01) | |

(52) U.S. Cl.
CPC .............. *A61K 6/887* (2020.01); *A61C 13/01* (2013.01); *A61K 6/00* (2013.01); *A61K 6/62* (2020.01)

(58) Field of Classification Search
CPC ....... A61K 6/083; A61K 6/0052; A61C 13/01
USPC ........................ 522/68, 6, 1, 189, 184; 520/1
See application file for complete search history.

(56) References Cited

U.S. PATENT DOCUMENTS

| | | | | |
|---|---|---|---|---|
| 5,009,597 A | * | 4/1991 | Schaefer | A61K 6/083 433/212.1 |
| 2005/0288387 A1 | * | 12/2005 | Feng | A61K 6/0017 523/113 |
| 2010/0076115 A1 | * | 3/2010 | Utterodt | A61K 6/887 523/116 |
| 2010/0240853 A1 | * | 9/2010 | Neffgen | A61K 6/083 526/328 |
| 2012/0129973 A1 | * | 5/2012 | Sun | A61K 6/02 523/115 |
| 2013/0078594 A1 | * | 3/2013 | Leslie-Martin | A61C 7/08 433/6 |
| 2014/0131908 A1 | | 5/2014 | Sun et al. | |
| 2015/0038634 A1 | | 2/2015 | Sun et al. | |
| 2016/0167301 A1 | * | 6/2016 | Cole | B33Y 70/00 425/174.4 |

FOREIGN PATENT DOCUMENTS

| | | |
|---|---|---|
| JP | H0678937 A | 3/1994 |
| JP | 460311 B2 | 10/2008 |
| JP | 2016505525 A | 2/2016 |
| WO | 2015017556 A1 | 2/2015 |

OTHER PUBLICATIONS

International Search Report (with English translation) and Written Opinion issued in corresponding International Patent Application No. PCT/ JP2017/028150, dated Oct. 17, 2017, 8 pages.
The Extended European Search Report dated Mar. 11, 2020, by the European Patent Office in corresponding European Patent Application No. 17837045.8. (6 pages).

* cited by examiner

*Primary Examiner* — Jessica Whiteley
(74) *Attorney, Agent, or Firm* — Buchanan Ingersoll & Rooney PC

(57) ABSTRACT

A photocurable composition for manufacturing a dental prosthesis by stereolithography, including: a photopolymerization initiator; and a (meth)acrylic monomer component including an acrylic monomer (X) having no aromatic rings and having a ring structure other than an aromatic ring and two or more acryloyloxy groups in one molecule and having an Mw of from 200 to 800, and at least one of a (meth) acrylic monomer (A) having one or more ether bonds and two (meth)acryloyloxy groups in one molecule and having a defined Mw, a (meth)acrylic monomer (B) having a ring structure other than an aromatic ring and one (meth)acryloyloxy group in one molecule and having a defined Mw, a (meth)acrylic monomer (C) having a hydrocarbon skeleton and two (meth)acryloyloxy groups in one molecule and having a defined Mw, and a (meth)acrylic monomer (D) having one or more aromatic rings and one (meth)acryloyloxy group in one molecule and having a Mw.

22 Claims, No Drawings

PHOTOCURABLE COMPOSITION, DENTURE BASE, AND PLATE DENTURE

TECHNICAL FIELD

The present invention relates to a photocurable composition, a denture base, and a plate denture.

BACKGROUND ART

Conventionally, plastic denture bases (called "resin bases") have been made by a method in which, first, a plaster mold adapted to the intraoral shape of a patient is prepared by a dental technique, then a curable resin is poured into the plaster mold, and then the curable resin is cured.

In recent years, as a method of reducing the number of times a patient comes to dentistry and efficiently manufacturing a denture base, in addition to the above-mentioned method using a plaster mold, a method of measuring the intraoral shape of a patient by three-dimensional measurement and manufacturing a denture base based on the measurement result has also been proposed (for example, see the following Patent Document 1). A method of manufacturing a dental prosthesis using a 3D printer has also been disclosed (for example, see the following Patent Document 2).

Patent Document 1 Japanese Patent Application Laid-Open (JP-A) No. 06-78937
Patent Document 2 Japanese Patent No. 4160311

SUMMARY OF INVENTION

Technical Problem

One of examples of a method of manufacturing a dental prosthesis, a medical instrument used intraorally, or a tooth jaw model (hereinafter, collectively referred to as "dental prosthesis or the like") using a 3D printer include a method called "stereolithography" for manufacturing a dental prosthesis by shaping a photocurable composition into a shape of a dental prosthesis or the like and photocuring the obtained shaped article.

When a dental prosthesis or the like (especially denture base) is manufactured by stereolithography, considering the practical utility of the dental prosthesis or the like, a photocurable composition after photocuring is demanded to have excellent flexural strength (bending strength) and flexural modulus. Furthermore, in this case, considering the durability of the dental prosthesis or the like, it is also demanded that the photocurable composition after photocuring has excellent Charpy impact strength.

An object of an embodiment of the invention is to provide a photocurable composition which is used for manufacturing a dental prosthesis, a medical instrument used intraorally, or a tooth jaw model by stereolithography, and which is excellent in flexural strength, flexural modulus, and Charpy impact strength after photocuring.

Another object of an embodiment of the invention is to provide a denture base which is produced using the photocurable composition and which is excellent in flexural strength, flexural modulus, and Charpy impact strength, and a plate denture including the denture base.

Solution to Problem

The inventors intensively studied to find that a photocurable composition including a combination of specific monomer species is excellent in flexural strength, flexural modulus, and Charpy impact strength after photocuring and is particularly suitable for manufacturing a dental prosthesis or the like (i.e., a dental prosthesis, a medical instrument used intraorally, or a tooth jaw model) by stereolithography, thereby completing the invention.

In other words, specific means for solving the problems are as follows.

<1> A photocurable composition which is used for manufacturing a dental prosthesis, a medical instrument used intraorally, or a tooth jaw model by stereolithography, the photocurable composition containing a (meth)acrylic monomer component and a photopolymerization initiator, wherein the (meth)acrylic monomer component comprises:

an acrylic monomer (X), which is at least one selected from acrylic monomers having no aromatic rings and having a ring structure other than an aromatic ring and two or more acryloyloxy groups in one molecule, and which has a weight average molecular weight of from 200 to 800, and at least one selected from the group consisting of: a (meth)acrylic monomer (A) which is at least one selected from di(meth)acrylic monomers having no aromatic rings and having one or more ether bonds and two (meth)acryloyloxy groups in one molecule, and which has a weight average molecular weight of from 200 to 400; a (meth) acrylic monomer (B), which is at least one selected from (meth)acrylic monomers having no aromatic rings and having a ring structure other than an aromatic ring and one (meth)acryloyloxy group in one molecule, and which has a weight average molecular weight of from 130 to 240; a (meth)acrylic monomer (C) which is at least one selected from di(meth)acrylic monomers having no aromatic rings and no ether bonds and having a hydrocarbon skeleton and two (meth)acryloyloxy groups in one molecule, and which has a weight average molecular weight of from 190 to 280; and a (meth)acrylic monomer (D) which is at least one selected from (meth)acrylic monomers having one or more aromatic rings and one (meth)acryloyloxy group in one molecule, and which has a weight average molecular weight of from 140 to 350.

<2> The photocurable composition according to <1>, wherein the (meth)acrylic monomer component comprises:

the acrylic monomer (X); and at least one selected from the group consisting of the (meth)acrylic monomer (A), the (meth)acrylic monomer (B), and the (meth)acrylic monomer (C).

<3> The photocurable composition according to <1> or <2>, wherein at least one acrylic monomer constituting the acrylic monomer (X) is an acrylic monomer having one or more ring structures selected from the group consisting of an alicyclic ring structure having from 5 to 20 carbon atoms and a heterocyclic ring structure in which a number of atoms constituting the ring is from 5 to 20, and two or more acryloyloxy groups.

<4> The photocurable composition according to any one of <1> to <3>, wherein at least one acrylic monomer constituting the acrylic monomer (X) is an acrylic monomer having one or more ring structures selected from the group consisting of a tetrahydrodicyclopentadienyl skeleton, a cyclohexane skeleton, an isocyanur skeleton, and a 1,3-dioxane skeleton, and two or more acryloyloxy groups.

<5> The photocurable composition according to any one of <1> to <4>, wherein at least one di(meth)acrylic monomer constituting the (meth)acrylic monomer (A) is a compound represented by the following Formula (a-1):

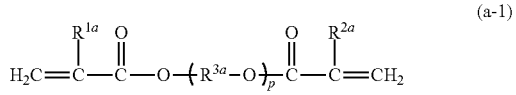

(a-1)

wherein, in Formula (a-1), each of $R^{1a}$ and $R^{2a}$ independently represents a hydrogen atom or a methyl group, $R^{3a}$ represents a linear or branched alkylene group having from 2 to 4 carbon atoms, and p represents from 2 to 4.

<6> The photocurable composition according to any one of <1> to <5>, wherein at least one di(meth)acrylic monomer constituting the (meth)acrylic monomer (A) is a compound represented by the following Formula (a-2):

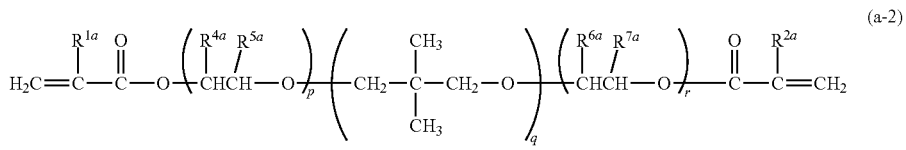

(a-2)

wherein, in Formula (a-2), each of $R^{1a}$, $R^{2a}$, $R^{4a}$, $R^{5a}$, $R^{6a}$, and $R^{7a}$ independently represents a hydrogen atom or a methyl group, each of p, q, and r independently represents 0 or 1, and p+q+r≥2 is satisfied.

<7> The photocurable composition according to any one of <1> to <6>, wherein at least one (meth)acrylic monomer constituting the (meth)acrylic monomer (B) is a compound represented by the following Formula (b-1):

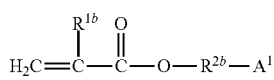

(b-1)

wherein, in Formula (b-1), $R^{1b}$ represents a hydrogen atom or a methyl group, $R^{2b}$ represents a single bond or a methylene group, and $A^1$ represents a ring structure other than an aromatic ring.

<8> The photocurable composition according to any one of <1> to <7>, wherein at least one (meth)acrylic monomer constituting the (meth)acrylic monomer (B) is a compound represented by the following Formula (b-2):

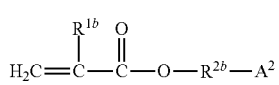

(b-2)

wherein, in Formula (b-2), $R^{1b}$ represents a hydrogen atom or a methyl group, $R^{2b}$ represents a single bond or a methylene group, and $A^2$ represents a ring structure having a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton.

<9> The photocurable composition according to any one of <1> to <8>, wherein at least one di(meth)acrylic monomer constituting the (meth)acrylic monomer (C) is a compound represented by the following Formula (c-1):

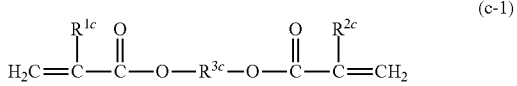

(c-1)

wherein, in Formula (c-1), each of $R^{1c}$ and $R^{2c}$ independently represents a hydrogen atom or a methyl group, and $R^{3c}$ represents an alkylene group having from 1 to 9 carbon atoms.

<10> The photocurable composition according to any one of <1> to <9>, wherein at least one di(meth)acrylic monomer constituting the (meth)acrylic monomer (C) is a compound represented by the following Formula (c-2):

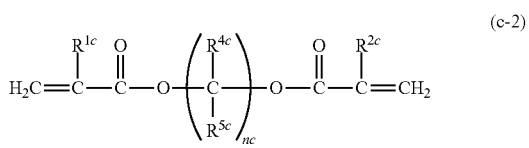

(c-2)

wherein, in Formula (c-2), each of $R^{1c}$ and $R^{2c}$ independently represents a hydrogen atom or a methyl group, each of $R^{4c}$ and $R^{5c}$ independently represents a hydrogen atom or a methyl group, nc represents from 1 to 9, and the alkylene group represented by $-(CR^{4c}R^{5c})_{nc}-$ has from 1 to 9 carbon atoms.

<11> The photocurable composition according to any one of <1> to <10>, wherein at least one of (meth)acrylic monomers constituting the (meth)acrylic monomer (D) is a compound represented by the following Formula (d-1):

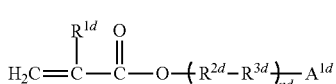

(d-1)

wherein, in Formula (d-1), $R^{1d}$ represents a hydrogen atom or a methyl group, $R^{2d}$ represents a single bond or a linear or branched alkylene group having from 1 to 5 carbon atoms, $R^{3d}$ represents a single bond, an ether bond (—O—), an ester bond (—O—(C=O)—), or —$C_6H_4$—O—, $A^{1d}$ represents an aromatic ring which may have a substituent, and nd represents from 1 to 2.

<12> The photocurable composition according to any one of <1> to <11>, wherein
the photopolymerization initiator is at least one selected from the group consisting of an alkyl phenone compound and an acylphosphine oxide compound.
<13> The photocurable composition according to any one of <1> to <12>, wherein
a content of the acrylic monomer (X), with respect to 1000 parts by mass of a total content of the (meth)acrylic monomer component, is from 250 parts by mass to 850 parts by mass.
<14> The photocurable composition according to any one of <1> to <13>, wherein
a content of the (meth)acrylic monomer (A), with respect to 1000 parts by mass of a total content of the (meth)acrylic monomer component, is from 100 parts by mass to 450 parts by mass.
<15> The photocurable composition according to any one of <1> to <14>, wherein
a content of the (meth)acrylic monomer (B), with respect to 1000 parts by mass of a total content of the (meth)acrylic monomer component, is from 100 parts by mass to 450 parts by mass.
<16> The photocurable composition according to any one of <1> to <15>, wherein
a content of the (meth)acrylic monomer (C), with respect to 1000 parts by mass of a total content of the (meth)acrylic monomer component, is from 100 parts by mass to 450 parts by mass.
<17> The photocurable composition according to any one of <1> to <16>, wherein
a content of the (meth)acrylic monomer (D), with respect to 1000 parts by mass of a total content of the (meth)acrylic monomer component, is from 300 parts by mass to 750 parts by mass.
<18> The photocurable composition according to any one of <1> to <17>, wherein
a content of the photopolymerization initiator, with respect to 1000 parts by mass of a total content of the (meth)acrylic monomer component, is from 1 part by mass to 50 parts by mass.
<19> The photocurable composition according to any one of <1> to <18>, wherein
a viscosity measured using an E type viscometer at 25° C. and at 50 rpm is from 20 mPa·s to 1500 mPa·s.
<20> The photocurable composition according to any one of <1> to <19>, wherein
a content of bisphenol A is 2.5 ppm or less.
<21> The photocurable composition according to any one of <1> to <20>, which is used for manufacturing a denture base or a mouthpiece by stereolithography.
<22> The photocurable composition according to any one of <1> to <21>, which is used for manufacturing a denture base by stereolithography.
<23> A denture base which is a cured product of the photocurable composition according to <22>.
<24> A plate denture comprising: the denture base according to <23>; and an artificial tooth fixed to the denture base.

Advantageous Effects of Invention

According to an embodiment of the invention, a photocurable composition which is used for manufacturing a dental prosthesis, a medical instrument used intraorally, or a tooth jaw model by stereolithography, and which is excellent in flexural strength, flexural modulus, and Charpy impact strength after photocuring is provided.

According to an embodiment of the invention, a denture base which is produced by stereolithography using the photocurable composition and which is excellent in flexural strength, flexural modulus, and Charpy impact strength, and a plate denture including the denture base are provided.

DESCRIPTION OF EMBODIMENTS

Hereinafter, an embodiment of the present invention (hereinafter, also referred to as "present embodiment") will be described.

Herein, a numerical range expressed by "from A to B" means a range including the numerical value A as a lower limit value and the numerical value B as an upper limit value.

Herein, the term "ether bond" means a bond (a bond represented by —O—) bonding two hydrocarbon groups by an oxygen atom, as usually defined. "—O—" in an ester bond (—C(=O)—O—) therefore does not fall under "ether bond".

Herein, "(meth)acrylate" represents acrylate or methacrylate, and "a (meth)acryloyloxy group" represents an acryloyloxy group or a methacryloyloxy group.

[Photocurable Composition]

The photocurable composition of the present embodiment is
a photocurable composition which is used for manufacturing a dental prosthesis, a medical instrument used intraorally, or a tooth jaw model by stereolithography,
the photocurable composition containing a (meth)acrylic monomer component and a photopolymerization initiator,
wherein the (meth)acrylic monomer component includes:
an acrylic monomer (X) which is at least one selected from acrylic monomers having no aromatic rings and having a ring structure other than an aromatic ring and two or more acryloyloxy groups in one molecule and which has a weight average molecular weight of from 200 to 800, and
at least one selected from the group consisting of: a (meth)acrylic monomer (A) which is at least one selected from di(meth)acrylic monomers having no aromatic rings and having one or more ether bonds and two (meth)acryloyloxy groups in one molecule and which has a weight average molecular weight of from 200 to 400; a (meth)acrylic monomer (B) which is at least one (meth)acrylic monomer having no aromatic rings and having a ring structure other than an aromatic ring and one (meth)acryloyloxy group in one molecule and which has a weight average molecular weight of from 130 to 240; a (meth)acrylic monomer (C) which is at least one selected from di(meth)acrylic monomers having no aromatic rings and no ether bonds and having a hydrocarbon skeleton and two (meth)acryloyloxy groups in one molecule and which has a weight average molecular weight of from 190 to 280; and a (meth)acrylic monomer (D) which is at least one selected from (meth)acrylic monomers having one or more aromatic rings and one (meth)acryloyloxy group in one molecule and which has a weight average molecular weight of from 140 to 350.

Since the photocurable composition of the embodiment contains a combination of an acrylic monomer (X) and at least one selected from the group consisting of a (meth)acrylic monomer (A), a (meth)acrylic monomer (B), a (meth)acrylic monomer (C), and a (meth)acrylic monomer (D) (hereinafter, also referred to as "at least one of (meth) acrylic monomers (A) to (D)"), the photocurable composition is excellent in flexural strength, flexural modulus, and Charpy impact strength after photocuring.

Therefore, a dental prosthesis or the like (especially a denture base) manufactured by stereolithography using the photocurable composition of the embodiment is also excellent in flexural strength, flexural modulus, and Charpy impact strength.

Furthermore, the photocurable composition of the embodiment has a viscosity suitable for manufacturing a dental prosthesis or the like by stereolithography.

In the embodiment, "(meth)acrylic monomer component" refers to an entire (meth)acrylic monomer contained in a photocurable composition of the embodiment.

"(Meth)acrylic monomer component" includes at least an acrylic monomer (X) and at least one of (meth)acrylic monomers (A) to (D).

Another (meth)acrylic monomer other than such an acrylic monomer (X) and such (meth)acrylic monomers (A) to (D) may be contained in a "(meth)acrylic monomer component", if necessary.

"(Meth)acrylic monomer component" may be configured to include at least one of an acrylic monomer (X) and (meth)acrylic monomers (A) to (C).

The photocurable composition of the embodiment preferably includes the following first to fourth aspects.

In the first aspect, the (meth)acrylic monomer component of the embodiment includes at least an acrylic monomer (X) and a (meth)acrylic monomer (A).

In the second aspect, the (meth)acrylic monomer component of the embodiment includes at least an acrylic monomer (X) and a (meth)acrylic monomer (B).

In the third aspect, the (meth)acrylic monomer component of the embodiment includes at least an acrylic monomer (X) and a (meth)acrylic monomer (C).

In the fourth aspect, the (meth)acrylic monomer component of the embodiment includes at least an acrylic monomer (X) and a (meth)acrylic monomer (D).

An overlapping portion may exist in at least two of the range of the first aspect, the range of the second aspect, the range of the third aspect, and the range of the fourth aspect.

For example, an embodiment in which a (meth)acrylic monomer component includes an acrylic monomer (X), a (meth)acrylic monomer (A), a (meth)acrylic monomer (B), a (meth)acrylic monomer (C), and a (meth)acrylic monomer (D) falls under any of the first to fourth aspects.

Since the photocurable composition of the embodiment (or, first to fourth aspects of the embodiment, which applies hereinafter) contains an acrylic monomer (X), the Charpy impact strength after photocuring is improved as compared to a case in which a methacrylic monomer having no aromatic ring and having a ring structure other than an aromatic ring and two or more methacryloyloxy groups in one molecule or an acrylic monomer having no ring structures in one molecule is contained instead of the acrylic monomer (X).

Since the photocurable composition of the embodiment contains an acrylic monomer (X), the flexural strength and flexural modulus after photocuring are improved as compared to a case in which an acrylic monomer having no aromatic rings and having a ring structure other than an aromatic ring and two or more acryloyloxy groups in one molecule and which has a weight average molecular weight of more than 800 is contained instead of the acrylic monomer (X).

The lower limit of the weight average molecular weight of the acrylic monomer (X), 200, is the lower limit provided in consideration of ease of production or availability of monomers.

Since the photocurable composition of the embodiment contains at least one of (meth)acrylic monomers (A) to (D) in addition to the acrylic monomer (X), the Charpy impact strength is improved.

More specifically, the photocurable composition of the first aspect of the embodiment is a photocurable composition of an aspect in which a (meth)acrylic monomer component contains at least an acrylic monomer (X) and a (meth)acrylic monomer (A) as described above.

Here, the (meth)acrylic monomer (A) is a (meth)acrylic monomer which is at least one selected from di(meth)acrylic monomers having no aromatic rings and having one or more ether bonds and two (meth)acryloyloxy groups in one molecule and has a weight average molecular weight of from 200 to 400 as described above.

In the photocurable composition of the first aspect, the flexural strength and flexural modulus after photocuring are improved as compared to a photocurable composition in which the (meth)acrylic monomer (A) in the first aspect is changed to a (meth)acrylic monomer having no aromatic rings and having one or more ether bonds and two (meth)acryloyloxy groups in one molecule and which has a weight average molecular weight of more than 400 which does not fall under any of the first to fourth aspects.

The lower limit of the weight average molecular weight of the (meth)acrylic monomer (A), 200, is the lower limit provided in consideration of ease of production or availability of monomers.

The photocurable composition of the second aspect of the embodiment is a photocurable composition of an aspect in which a (meth)acrylic monomer component contains at least an acrylic monomer (X) and a (meth)acrylic monomer (B) as described above.

Here, the (meth)acrylic monomer (B) is a (meth)acrylic monomer which is at least one selected from (meth)acrylic monomers having no aromatic rings and having a ring structure other than an aromatic ring and one (meth)acryloyloxy group in one molecule and has a weight average molecular weight of from 130 to 240 as described above.

In the photocurable composition of the second aspect, the flexural strength and flexural modulus after photocuring are improved as compared to a photocurable composition in which the (meth)acrylic monomer (B) in the second aspect is changed to a (meth)acrylic monomer having no ring structures and having one (meth)acryloyloxy groups in one molecule and which has a weight average molecular weight of more than 240 which does not fall under any of the first to fourth aspects.

The lower limit of the weight average molecular weight of the (meth)acrylic monomer (B), 130, is the lower limit provided in consideration of ease of production or availability of monomers.

The photocurable composition of the third aspect of the embodiment is a photocurable composition of an aspect in which a (meth)acrylic monomer component contains at least an acrylic monomer (X) and a (meth)acrylic monomer (C) as described above.

Here, the (meth)acrylic monomer (C) is a (meth)acrylic monomer which is at least one selected from di(meth)acrylic monomers having no aromatic rings and no ether bonds and having a hydrocarbon skeleton and two (meth)acryloyloxy groups in one molecule and has a weight average molecular weight of from 190 to 280 as described above.

In the photocurable composition of the third aspect, the flexural strength and flexural modulus after photocuring are improved as compared to a photocurable composition in which the (meth)acrylic monomer (C) in the third aspect is changed to a (meth)acrylic monomer having no aromatic rings and no ether bonds and having two (meth)acryloyloxy groups in one molecule and which has a weight average molecular weight of more than 280 which does not fall under any of the first to fourth aspects.

The lower limit of the weight average molecular weight of the (meth)acrylic monomer (C), 190, is the lower limit provided in consideration of ease of production or availability of monomers.

The photocurable composition of the fourth aspect of the embodiment is a photocurable composition of an aspect in which a (meth)acrylic monomer component contains at least an acrylic monomer (X) and a (meth)acrylic monomer (D) as described above.

Here, the (meth)acrylic monomer (D) is a (meth)acrylic monomer which is at least one selected from (meth)acrylic monomers having one or more aromatic rings and one (meth)acryloyloxy group in one molecule and has a weight average molecular weight of from 140 to 350 as described above.

In the photocurable composition of the fourth aspect, the flexural strength and flexural modulus after photocuring are improved as compared to a photocurable composition in which the (meth)acrylic monomer (D) in the fourth aspect is changed to a (meth)acrylic monomer having one or more aromatic rings and one (meth)acryloyloxy groups in one molecule and which has a weight average molecular weight of more than 350 which does not fall under any of the first to fourth aspects.

The lower limit of the weight average molecular weight of the (meth)acrylic monomer (D), 140, is the lower limit provided in consideration of ease of production or availability of monomers.

From the viewpoint of the practical utility of the resulting dental prosthesis or the like (especially the denture base), the photocurable composition of the embodiment preferably satisfies the following flexural strength (bending strength) and the following flexural modulus after photocuring.

In other words, when the photocurable composition of the embodiment is formed into a size of 64 mm×10 mm×3.3 mm in thickness to obtain a molded article, the obtained molded article is irradiated with ultraviolet rays under the condition of 5 J/cm$^2$ and photocured to obtain a stereolithography product (or a cured product, which applies hereinafter), the obtained stereolithography product is stored in a thermostatic water bath at 37±1° C. for 50±2 hours, and the flexural strength (bending strength) is measured after the storage in accordance with ISO20795-1:2008 (or JIS T 6501:2012), the flexural strength is preferably 60 MPa or more, and more preferably 65 MPa or more. The flexural strength may be 95 MPa or less, or may be 85 MPa or less.

When the photocurable composition of the embodiment is formed into a size of 64 mm×10 mm×3.3 mm in thickness to obtain a molded article, the obtained molded article is irradiated with ultraviolet rays under the condition of 5 J/cm$^2$ and photocured to obtain a stereolithography product, the obtained stereolithography product is stored in a thermostatic water bath at 37±1° C. for 50±2 hours, and the flexural modulus is measured after the storage in accordance with ISO20795-1:2008 (or JIS T 6501:2012), the flexural modulus is preferably 1500 MPa or more, and more preferably 2000 MPa or more. The flexural modulus may be 3500 MPa or less, or may be 3000 MPa or less.

The photocurable composition of the embodiment preferably satisfies the following Charpy impact strength from the viewpoint of the durability of a resulting dental prosthesis or the like (especially a denture base).

In other words, when the photocurable composition of the embodiment is formed into a size of 80 mm×10 mm×4 mm in thickness to obtain a molded article, the obtained molded article is irradiated with ultraviolet rays under the condition of 5 J/cm$^2$ and photocured to obtain a stereolithography product, the obtained stereolithography product is stored in a thermostatic water bath at 37±1° C. for 50±2 hours, a notch of shape A having a depth of 2 mm is provided in a longitudinal center portion of the stereolithography product after storage to prepare a single notched test piece, and the Charpy impact strength of the obtained single notched test piece is measured in accordance with ISO179-1:2010 (or JIS K 7111-1:2012) under the conditions of a hammer capacity of 0.5 J, a swing angle of 148°, a test temperature of 23° C., and an edgewise impact, the Charpy impact strength is preferably 1.0 kJ/m$^2$ or more. The Charpy impact strength may be 3.0 kJ/m$^2$ or less.

The photocurable composition of the embodiment is used for manufacturing a dental prosthesis or the like (or, a dental prosthesis, a medical instrument used intraorally, or a tooth jaw model) by stereolithography.

In the embodiment, examples of the dental prosthesis include a denture base, a denture, an inlay, a crown, a bridge, a temporary crown, and a temporary bridge. Among them, a denture base is preferable.

In the embodiment, examples of medical instruments used intraorally include an orthodontic appliance (such as a mouthpiece or an orthodontic appliance), an occlusal splint, a tray for impression, and a surgical guide. Among them, an orthodontic appliance is preferable, and a mouthpiece is more preferable.

As a dental prosthesis or the like (or, a dental prosthesis, a medical instrument used intraorally, or a tooth jaw model), a dental prosthesis or an orthodontic appliance is preferable, a denture base or a mouthpiece is more preferable, and a denture base is particularly preferable.

In the embodiment, "stereolithography" is one type of three-dimensional modeling method using a 3D printer.

Examples of the stereolithography method include an SLA (Stereo Lithography Apparatus) method, a DLP (Digital Light Processing) method, and an ink jet method.

The photocurable composition of the embodiment is particularly suitable for stereolithography of an SLA method or a DLP method.

Examples of the SLA method include a method of obtaining a three-dimensional product by irradiating a photocurable composition with a spot ultraviolet laser beam.

When a dental prosthesis or the like is manufactured by the SLA method, for example, a layering operation in which the photocurable composition of the embodiment is stored in a container, the liquid surface of the photocurable composition is selectively irradiated with a spot ultraviolet laser beam in such a manner to obtain a desired pattern to cure the photocurable composition, a cured layer having a desired thickness is formed on a shaping table, the modeling table is then lowered, and a liquid photocurable composition for one layer is provided onto the cured layer and cured in the same manner as above to obtain a continuous cured layer may be repeated. A dental prosthesis or the like can thus be manufactured.

Examples of the DLP method include a method of obtaining a three-dimensional product by irradiating a photocurable composition with a planar light.

Regarding the method of obtaining a three-dimensional product by the DLP method, for example, descriptions in Japanese Patent No. 5111880 and Japanese Patent No. 5235056 can be appropriately referred to.

When a dental prosthesis or the like is manufactured by the DLP method, for example, a lamp that emits light other than laser light such as a high pressure mercury lamp, a super high pressure mercury lamp, or a low pressure mercury lamp, an LED, or the like is used as a light source, a planar drawing mask in which a plurality of digital micromirror shutters are arranged in a planar shape is arranged between the light source and a forming surface of a photocurable composition, and a cured layer having a predetermined shape pattern may be sequentially layered by irradiating the forming surface of the photocurable composition with light through the planar drawing mask. A dental prosthesis or the like can thus be manufactured.

Examples of the inkjet method include a method of continuously ejecting droplets of a photocurable composition from an inkjet nozzle onto a substrate and irradiating the droplets adhering to the substrate with light to obtain a three-dimensional product.

When a dental prosthesis or the like is manufactured by an inkjet method, for example, an operation in which a photocurable composition is ejected from the inkjet nozzle onto the substrate while a head with an inkjet nozzle and a light source is scanned in a plane, and the ejected photocurable composition is irradiated with light to form a cured layer may be repeated to sequentially layer cured layers. A dental prosthesis or the like can thus be manufactured.

From the viewpoint of suitability for manufacturing a dental prosthesis or the like by stereolithography, the photocurable composition of the embodiment preferably has a viscosity measured with an E type viscometer at 25° C. at 50 rpm of from 20 mPa·s to 1500 mPa·s. The lower limit of the viscosity is more preferably 50 mPa·s. The upper limit of the viscosity is more preferably 1000 mPa·s, and still more preferably 500 mPa·s.

The viscosity of the photocurable composition of the embodiment at 25° C. and at 50 rpm may be adjusted according to the method of stereolithography.

For example, when a dental prosthesis or the like is manufactured by an SLA method, the viscosity is preferably from 50 mPa·s to 1500 mPa·s, and more preferably from 50 mPa·s to 1000 mPa·s.

For example, when a dental prosthesis or the like is manufactured by a DLP method, the viscosity is preferably from 50 mPa·s to 500 mPa·s, and more preferably from 50 mPa·s to 250 mPa·s.

For example, when a dental prosthesis or the like is manufactured by an inkjet method, the viscosity is preferably from 20 mPa·s to 500 mPa·s, and more preferably from 20 mPa·s to 100 mPa·s.

In the photocurable composition of the embodiment, the content of bisphenol A is preferably 2.5 ppm or less, more preferably 2.0 ppm or less, and still more preferably 1.0 ppm or less.

When the content of bisphenol A is 2.5 ppm or less, the photocurable composition of the embodiment can be advantageously used for public hygiene and dental materials.

Next, the components of the photocurable composition of the embodiment (or, the first to fourth aspects) will be described.

<Acrylic Monomer (X)>

The (meth)acrylic monomer component in the embodiment contains an acrylic monomer (X) which is at least one selected from acrylic monomers having no aromatic rings and having a ring structure other than an aromatic ring and two or more acryloyloxy groups in one molecule and has a weight average molecular weight of from 200 to 800.

The acrylic monomer (X) may be composed of only one of acrylic monomers having no aromatic rings and having a ring structure other than an aromatic ring and two or more acryloyloxy groups in one molecule or may be a mixture composed of two or more kinds of such acrylic monomers.

From the viewpoint of further improving the Charpy impact strength after photocuring, at least one of acrylic monomers constituting the acrylic monomer (X) preferably has one or more ether bonds in one molecule.

In detail, since at least one of the acrylic monomers constituting the acrylic monomer (X) has one or more ether bonds in one molecule, the degree of freedom of molecular motion increases, and the toughness is improved by imparting flexibility to the cured product after photocuring, and as a result, the Charpy impact strength of the cured product (or, the Charpy impact strength after photocuring of the photocurable composition) is improved.

More preferably, at least one of the acrylic monomers has eight or fewer ether bonds in one molecule.

In at least one of the acrylic monomers, when the number of ether bonds in one molecule is eight or less, the flexural strength and flexural modulus after photocuring are further improved.

From the viewpoint of further improving the flexural strength and flexural modulus after photocuring, the number of ether bonds in one molecule is preferably six or less, more preferably four or less, and still more preferably two or less.

Herein, the number of ether bonds in the acrylic monomer (X) does not include, when an ether bond is contained in a ring structure other than an aromatic ring, the number of ether bonds (for example, an ether bond possessed by a dioxane skeleton) contained in the ring structure other than an aromatic ring.

From the viewpoint of improving the Charpy impact strength, flexural strength, and flexural modulus, at least one of the acrylic monomers constituting the acrylic monomer (X) is preferably an acrylic monomer having two or three acryloyloxy groups.

From the viewpoint of improving the Charpy impact strength, flexural strength, and flexural modulus, at least one acrylic monomer constituting the acrylic monomer (X) is preferably an acrylic monomer having one or more ring structures selected from the group consisting of an alicyclic ring structure having from 5 to 20 carbon atoms and a heterocyclic ring structure in which the number of atoms constituting the ring is from 5 to 20 and two or more (preferably two or three) acryloyloxy groups.

From the viewpoint of further improving the Charpy impact strength, flexural strength, and flexural modulus, at least one acrylic monomer constituting the acrylic monomer (X) is more preferably an acrylic monomer having one or more ring structures selected from the group consisting of a tetrahydrodicyclopentadienyl skeleton, a cyclohexane skeleton, an isocyanuric skeleton, and a 1,3-dioxane skeleton and two or more (preferably two or three) acryloyloxy groups.

Specific examples of the acrylic monomer (X) include ethoxylated hydrogenated bisphenol A diacrylate (EO=2 mol, 4 mol), caprolactone-modified tris-(2-acryloxyethyl) isocyanurate triacrylate (CL=1 mol, 2 mol, 3 mol), dimethylol-tricyclodecane diacrylate, ethoxylated dimethylol-tricyclodecane diacrylate (EO=2 mol), dioxane glycol diacrylate, and cyclohexane dimethanol diacrylate.

In the photocurable composition of the embodiment, the content of the acrylic monomer (X) is, with respect to 1000 parts by mass of the total content of the (meth)acrylic monomer component, preferably from 250 parts by mass to 850 parts by mass, more preferably from 270 parts by mass to 830 parts by mass, and still more preferably from 300 parts by mass to 800 parts by mass. In particular, when (meth)acrylic monomers (A) to (C) are used, the content of the acrylic monomer (X) is, with respect to 1000 parts by mass of the total content of the (meth)acrylic monomer component, preferably from 550 parts by mass to 850 parts by mass, more preferably from 600 parts by mass to 830 parts by mass, and still more preferably from 620 parts by mass to 800 parts by mass. When the (meth)acrylic monomer (D) is used, the content of the acrylic monomer (X) is, with respect to 1000 parts by mass of the total content of the (meth)acrylic monomer component, preferably from 250 parts by mass to 650 parts by mass, more preferably from 270 parts by mass to 630 parts by mass, and still more preferably from 300 parts by mass to 600 parts by mass.

<(Meth)Acrylic Monomer (A)>

The (meth)acrylic monomer component in the first aspect of the embodiment is at least one selected from di(meth) acrylic monomers having no aromatic rings and having one or more ether bonds and two (meth)acryloyloxy groups in one molecule, and contains a (meth)acrylic monomer (A) which has a weight average molecular weight of from 200 to 400.

A (meth)acrylic monomer (A) may be contained in each of the (meth)acrylic monomer component in the second aspect, the (meth)acrylic monomer component in the third aspect, and the (meth)acrylic monomer component in the fourth aspect.

The (meth)acrylic monomer (A) may be composed of only one of di(meth)acrylic monomers having no aromatic rings and having one or more ether bonds and two (meth) acryloyloxy groups in one molecule, or may be a mixture of two or more kinds of these di(meth)acrylic monomers.

From the viewpoint of further improving the Charpy impact strength after photocuring, the number of ether bonds in one molecule of at least one di(meth)acrylic monomer constituting the (meth)acrylic monomer (A) is preferably from one to three, and more preferably one or two.

From the viewpoint of further improving the Charpy impact strength after photocuring, at least one di(meth) acrylic monomer constituting the (meth)acrylic monomer (A) is preferably a compound represented by the following Formula (a-1).

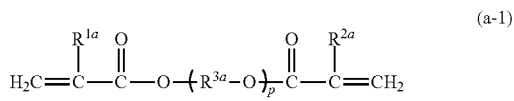

(a-1)

In Formula (a-1), each of $R^{1a}$ and $R^{2a}$ independently represent a hydrogen atom or a methyl group. $R^{3a}$ represents a linear or branched alkylene group having from 2 to 4 carbon atoms. p represents from 2 to 4.

In Formula (a-1), a plurality of $R^{3a}$ may be the same or different.

In Formula (a-1), p is preferably 2 or 3.

In Formula (a-1), $R^{1a}$ and $R^{2a}$ each are preferably a hydrogen atom or a methyl group.

$R^{3a}$ is preferably an ethylene group, a trimethylene group, a tetramethylene group, a 1-methylethylene group, a 1-ethylethylene group, a 2-methyltrimethylene group, or a 2,2-dimethyltrimethylene group, and more preferably an ethylene group, a 1-methylethylene group, or a 2,2-dimethyltrimethylene group.

At least one of di(meth)acrylic monomers constituting the (meth)acrylic monomer (A) is preferably a compound represented by the following Formula (a-2).

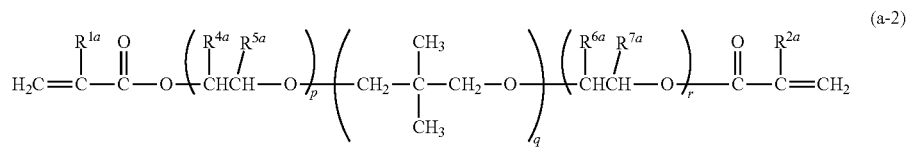

(a-2)

In Formula (a-2), each of $R^{1a}$, $R^{2a}$, $R^{4a}$, $R^{5a}$, $R^{6a}$, and $R^{7a}$ independently represent a hydrogen atom or a methyl group. Each of p, q, and r independently represent 0 or 1, and p+q+r≥2 is satisfied.

In Formula (a-2), $R^{1a}$ and $R^{ea}$ each are preferably a hydrogen atom or a methyl group. $R^{4a}$ and $R^{7a}$ each are preferably a hydrogen atom or a methyl group, and $R^{5a}$ and $R^{6a}$ each are preferably a hydrogen atom or a methyl group.

p and r each are preferably 1.

The weight average molecular weight of the (meth)acrylic monomer (A) is from 200 to 400.

The weight average molecular weight of the (meth)acrylic monomer (A) in the first aspect is preferably from 200 to 350.

When the (meth)acrylic monomer component in the second aspect, the third aspect, or the fourth aspect contains a (meth)acrylic monomer (A), the weight average molecular weight of the (meth)acrylic monomer (A) in the second aspect, the third aspect, or the fourth aspect is preferably from 200 to 350, more preferably from 250 to 350, and particularly preferably from 300 to 350.

Examples of the (meth)acrylic monomer (A) include diethylene glycol di(meth)acrylate, triethylene glycol di(meth)acrylate, dipropylene glycol di(meth)acrylate, tripropylene glycol di(meth)acrylate, and propoxylated neopentyl glycol di(meth)acrylate.

In the photocurable composition of the embodiment, the content of the (meth)acrylic monomer (A) is, with respect to 1000 parts by mass of the total content of the (meth)acrylic monomer component, preferably from 100 parts by mass to 450 parts by mass, more preferably from 150 parts by mass to 400 parts by mass, and particularly preferably from 180 parts by mass to 380 parts by mass.

When the (meth)acrylic monomer component in the first aspect contains at least one of the (meth)acrylic monomer (B) and the (meth)acrylic monomer (C) described below, the content of the (meth)acrylic monomer (A) with respect to the total content of the (meth)acrylic monomer (A), the (meth)acrylic monomer (B), and the (meth)acrylic monomer (C) is preferably 51% by mass or more.

When the (meth)acrylic monomer component in the first aspect contains at least one of the (meth)acrylic monomer (B), the (meth)acrylic monomer (C), and the (meth)acrylic monomer (D) described below, the content of the (meth)acrylic monomer (A) with respect to the total content of the (meth)acrylic monomer (A), the (meth)acrylic monomer (B), the (meth)acrylic monomer (C), and the (meth)acrylic monomer (D) is preferably 51% by mass or more.

<(Meth)Acrylic Monomer (B)>

The (meth)acrylic monomer component in the second aspect of the embodiment is at least one selected from (meth)acrylic monomers having no aromatic rings and having a ring structure other than an aromatic ring and one (meth)acryloyloxy group in one molecule and includes a (meth)acrylic monomer (B) which has a weight average molecular weight of from 130 to 240.

The (meth)acrylic monomer (B) may be contained in each of the (meth)acrylic monomer component in the first aspect, the (meth)acrylic monomer component in the third aspect, and the (meth)acrylic monomer component in the fourth aspect.

The (meth)acrylic monomer (B) may be composed of one of (meth)acrylic monomer having a ring structure other than an aromatic ring and one (meth)acryloyloxy group in one molecule, or may be a mixture of two or more kinds of the (meth)acrylic monomers.

In the (meth)acrylic monomer (B), the ring structure other than an aromatic ring is preferably an alicyclic structure or a heterocyclic structure.

More preferably, the ring structure other than an aromatic ring is a ring structure having a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton. The ring structure having such a skeleton may be substituted with a substituent such as an alkyl group (a methyl group, an ethyl group, a propyl group, a butyl group, or the like).

In the (meth)acrylic monomer (B), from the viewpoint of further improving the flexural strength and flexural modulus after photocuring, the ring structure other than an aromatic ring is preferably a polycyclic structure, more preferably a ring structure having a dicyclopentenyl skeleton, a dicyclopentanyl skeleton, a cyclohexane skeleton, an isobornyl skeleton, or a norbornyl skeleton.

From the viewpoint of suppressing water absorption, at least one (meth)acrylic monomer constituting the (meth)acrylic monomer (B) is preferably a compound not containing an imide structure.

At least one (meth)acrylic monomer constituting the (meth)acrylic monomer (B) is preferably a compound represented by the following Formula (b-1).

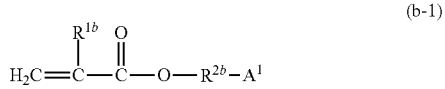

In Formula (b-1), $R^{1b}$ represents a hydrogen atom or a methyl group. $R^{2b}$ represents a single bond or a methylene group. $A^1$ represents a ring structure other than an aromatic ring.

In Formula (b-1), preferred ranges of "ring structure other than aromatic ring" represented by $A^1$ are as described above.

In other words, at least one (meth)acrylic monomer constituting the (meth)acrylic monomer (B) is more preferably a compound represented by the following Formula (b-2).

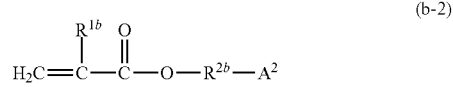

In Formula (b-2), $R^{1b}$ represents a hydrogen atom or a methyl group. $R^{2b}$ represents a single bond or a methylene group. $A^2$ represents a ring structure having a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton.

The weight average molecular weight of the (meth)acrylic monomer (B) is from 130 to 240.

The weight average molecular weight of the (meth)acrylic monomer (B) in the second aspect is preferably from 140 to 220.

When the (meth)acrylic monomer component in the first aspect, the third aspect, or the fourth aspect contains a (meth)acrylic monomer (B), the weight average molecular weight of the (meth)acrylic monomer (B) in the first aspect, the third aspect, or the fourth aspect is preferably from 150 to 240, and more preferably from 180 to 230.

Examples of the (meth)acrylic monomer (B) include isobornyl (meth)acrylate, norbornyl (meth)acrylate, dicyclopentenyl (meth)acrylate, dicyclopentanyl (meth)acrylate, cyclohexyl (meth)acrylate, tetrahydrofurfuryl (meth)acrylate, (meth)acryloyl morpholine, 4-tert-butylcyclohexanol (meth)acrylate, cyclohexane dimethanol di(meth)acrylate, (2-methyl-2-ethyl-1,3-dioxolan-4-yl) methyl acrylate, and cyclic trimethylolpropane formal acrylate.

In the photocurable composition of the embodiment, the content of the (meth)acrylic monomer (B) is, with respect to 1000 parts by mass of the total content of the (meth)acrylic monomer component, preferably from 100 parts by mass to 450 parts by mass, more preferably from 150 parts by mass to 400 parts by mass, and particularly preferably from 180 parts by mass to 380 parts by mass.

When the (meth)acrylic monomer component in the second aspect contains at least one of the (meth)acrylic monomer (A) and the (meth)acrylic monomer (C) described below, the content of the (meth)acrylic monomer (B) with respect to the total content of the (meth)acrylic monomer (A), the (meth)acrylic monomer (B), and the (meth)acrylic monomer (C) is preferably 51% by mass or more.

When the (meth)acrylic monomer component in the second aspect contains at least one of the (meth)acrylic monomer (A) described above, the (meth)acrylic monomer (C) and the (meth)acrylic monomer (D) described below, the content of the (meth)acrylic monomer (B) with respect to the total content of (meth)acrylic monomer (A), (meth)acrylic monomer (B), (meth)acrylic monomer (C), and (meth)acrylic monomer (D) is preferably 51% by mass or more.

<(Meth)Acrylic Monomer (C)>

In the third aspect of the embodiment, the (meth)acrylic monomer component contains at least one selected from di(meth)acrylic monomers having no aromatic rings and no ether bonds and having a hydrocarbon skeleton and two (meth)acryloyloxy groups in one molecule and contains a (meth)acrylic monomer (C) which has a weight average molecular weight of from 190 to 280.

The (meth)acrylic monomer (C) may be contained in each of the (meth)acrylic monomer component in the first aspect, the (meth)acrylic monomer component in the second aspect, and the (meth)acrylic monomer component in the fourth aspect.

The (meth)acrylic monomer (C) may be composed of only one of di(meth)acrylic monomers having no aromatic rings and no ether bonds and having a hydrocarbon skeleton and two (meth)acryloyloxy groups in one molecule, or may be a mixture of two or more kinds of the (meth)acrylic monomers.

From the viewpoint of further improving the flexural strength and flexural modulus after photocuring, at least one of di(meth)acrylic monomers constituting the (meth)acrylic monomer (C) is preferably a compound represented by the following Formula (c-1).

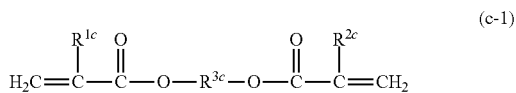

In Formula (c-1), each of $R^{1c}$ and $R^{2c}$ independently represent a hydrogen atom or a methyl group. $R^{3c}$ represents an alkylene group having from 1 to 9 carbon atoms.

The alkylene group represented by $R^{3c}$ may be a linear alkylene group or a branched alkylene group.

From the viewpoint of further improving the flexural strength and flexural modulus after photocuring, at least one di(meth)acrylic monomer constituting the (meth)acrylic monomer (C) is more preferably a compound represented by the following Formula (c-2).

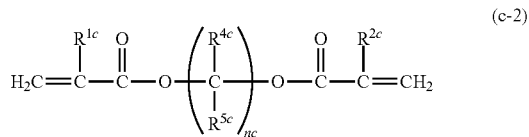

In Formula (c-2), each of $R^{1c}$ and $R^{2c}$ independently represent a hydrogen atom or a methyl group, each of $R^{4c}$ and $R^{5c}$ independently represent a hydrogen atom or a methyl group, and nc represents from 1 to 9. The alkylene group represented by $-(CR^{4c}R^{5c})^{nc}-$ has from 1 to 9 carbon atoms.

When a plurality of $R^{4c}$s are present in Formula (c-2), the plurality of $R^{4c}$s may be the same or different. The same applies to $R^{5c}$.

Specific examples of the (meth)acrylic monomer (C) include 1,3-butylene glycol diacrylate, neopentyl glycol diacrylate, 1,4-butanediol diacrylate, 1,4-butanediol dimethacrylate, 1,6-hexanediol diacrylate, 1,6-hexanediol dimethacrylate, 1,9-nonanediol diacrylate, ethylene glycol dimethacrylate, and 1,3-butylene glycol dimethacrylate.

In the photocurable composition of the embodiment, the content of the (meth)acrylic monomer (C) is, with respect to 1000 parts by mass of the total content of the (meth)acrylic monomer component, preferably from 100 parts by mass to 450 parts by mass, more preferably from 100 parts by mass to 400 parts by mass, and particularly preferably from 100 parts by mass to 350 parts by mass.

When the (meth)acrylic monomer component in the third aspect contains at least one of the (meth)acrylic monomer (A) and the (meth)acrylic monomer (B) described above, the content of the (meth)acrylic monomer (C) with respect to the total content of the (meth)acrylic monomer (A), the (meth)acrylic monomer (B), and the (meth)acrylic monomer (C) is preferably 51% by mass or more.

When the (meth)acrylic monomer component in the third aspect contains at least one of the (meth)acrylic monomer (A) and the (meth)acrylic monomer (B) described above, and the (meth)acrylic monomer (D) described below, the content of the (meth)acrylic monomer (C) with respect to the total content of (meth)acrylic monomer (A), (meth)acrylic monomer (B), (meth)acrylic monomer (C), and (meth)acrylic monomer (D) is preferably 51% by mass or more.

<(Meth)Acrylic Monomer (D)>

In the fourth aspect of the embodiment, the (meth)acrylic monomer component contains at least one selected from (meth)acrylic monomers having one or more aromatic rings and having one (meth)acryloyloxy group in one molecule and contains a (meth)acrylic monomer (D) which has a weight average molecular weight of from 140 to 350.

The (meth)acrylic monomer (D) may be contained in each of the (meth)acrylic monomer component in the first aspect, the (meth)acrylic monomer component in the second aspect, and the (meth)acrylic monomer component in the third aspect.

The (meth)acrylic monomer (D) may be composed of only one of di(meth)acrylic monomers having one or more aromatic rings and having one (meth)acryloyloxy group in one molecule, or may be a mixture of two or more kinds of the (meth)acrylic monomers.

The number of aromatic rings contained in one molecule of the (meth)acrylic monomer (D) is not particularly limited as long as the number is one or more, and the number is preferably 1 to 3, more preferably 1 or 2, and particularly preferably 2. When a plurality of aromatic rings are contained in one molecule, the types of aromatic rings may be the same or different from each other.

When the (meth)acrylic monomer component contains the (meth)acrylic monomer (D), the Charpy impact strength after photocuring is considerably improved.

In the (meth)acrylic monomer (D), the aromatic ring is preferably a phenyl group or a naphthyl group, and more preferably a phenyl group. The aromatic ring may have a substituent such as an alkyl group, an aryl group, an alkylaryl group, or an aryloxy group. The (meth)acrylic monomer (D) preferably has one or two ether bonds or ester bonds.

Examples of the (meth)acrylic monomer (D) include phenyl (meth)acrylate, benzyl (meth)acrylate, phenoxyethylene glycol (meth)acrylate, phenoxydiethylene glycol (meth)acrylate, 3-phenoxybenzyl (meth)acrylate, neopentyl glycol (meth)acrylic acid benzoic acid ester, 2-(o-phenylphenoxy) ethyl (meth)acrylate, 2-(1-naphthoxy) ethyl (meth)acrylate, p-cumylphenoxy polyethylene glycol (meth)acrylate, and nonylphenol EO-modified (meth)acrylate (EO=1 mol). Here, "EO-modified" means having a structure of an ethylene oxide unit ($-CH_2-CH_2-O-$).

From the viewpoint of further improving the Charpy impact strength after photocuring, at least one of (meth)acrylic monomers constituting the (meth)acrylic monomer (D) is preferably a compound represented by the following Formula (d-1).

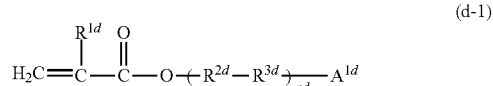

In Formula (d-1), $R^{1d}$ represents a hydrogen atom or a methyl group. $R^{2d}$ represents a single bond or a linear or branched alkylene group having from 1 to 5 carbon atoms. $R^{3d}$ represents a single bond, an ether bond (—O—), an ester bond (—O—(C=O)—), or —$C_6H_4$—O—. $A^{1d}$ represents an aromatic ring which may have a substituent. nd represents from 1 to 2. Examples of the substituent on the aromatic ring of $A^{1d}$ include an alkyl group (a methyl group, an ethyl group, a propyl group, a butyl group, or the like), an aryl group, an alkylaryl group, and an aryloxy group.

Examples of the aromatic ring which optionally have a substituent in $A^{1d}$ include a phenyl group, a phenyl ether group, a biphenyl group, a terpenyl group, a benzhydryl group, a diphenylamino group, a benzophenone group, a naphthyl group, an anthracenyl group, a phenanthrenyl group, a tolyl group, a xylyl group, a mesityl group, a cumyl group, a styryl group, and a nonylphenyl group.

The aromatic ring in $A^{1d}$ is preferably a phenyl group, a phenyl ether group, a biphenyl group, a naphthyl group, a cumyl group or a nonylphenyl group, and more preferably a phenyl group or a biphenyl group.

In Formula (d-1), one or two ether bonds or ester bonds are preferably contained.

Examples of a linear or branched alkylene group having from 1 to 5 carbon atoms represented by $R^{2d}$ include a methylene group, an ethylene group, an n-propylene group, an isopropylene group, an n-butylene group, an isobutylene group, a sec-butylene group, a tert-butylene group, an n-pentylene group, an isopentylene group, a neopentylene group, a sec-pentylene group, a tert-pentylene group, and a 3-pentylene group. Among them, $R^{2d}$ is preferably a single bond, a methylene group, or an ethylene group.

$R^{3d}$ is preferably an ether bond or —$C_6H_4$—O—.

The weight average molecular weight of the (meth)acrylic monomer (D) is from 140 to 350, preferably from 160 to 300, more preferably from 180 to 270, and particularly preferably from 200 to 270.

Specific examples of the (meth)acrylic monomer (D) include ethoxylated o-phenylphenol (meth)acrylate, ethoxylated o-phenylphenol EO-modified (meth)acrylate, ethoxylated p-cumyl phenol (meth)acrylate, ethoxylated p-nonylphenol (meth)acrylate, ethoxylated p-methylphenol (meth)acrylate, neopentyl glycol-acrylic acid-benzoic acid ester, benzyl (meth)acrylate, m-phenoxybenzyl (meth)acrylate, 2-(1-naphthoxy) ethyl (meth)acrylate.

In the photocurable composition of the embodiment, the content of the (meth)acrylic monomer (D) is, with respect to 1000 parts by mass of the total content of the (meth)acrylic monomer component, preferably from 350 parts by mass to 750 parts by mass, more preferably from 370 parts by mass to 730 parts by mass, and particularly preferably from 400 parts by mass to 700 parts by mass.

When the (meth)acrylic monomer component in the fourth aspect contains at least one of the (meth)acrylic monomer (A), the (meth)acrylic monomer (B) and the (meth)acrylic monomer (C) described above, the content of the (meth)acrylic monomer (D) with respect to the total content of (meth)acrylic monomer (A), (meth)acrylic monomer (B), (meth)acrylic monomer (C), and (meth)acrylic monomer (D) is preferably 51% by mass or more.

The (meth)acrylic monomer component may contain another (meth)acrylic monomer other than the acrylic monomer (X), the (meth)acrylic monomer (A), the (meth)acrylic monomer (B), the (meth)acrylic monomer (C), and the (meth)acrylic monomer (D).

In the (meth)acrylic monomer component, the total content of the acrylic monomer (X), the (meth)acrylic monomer (A), the (meth)acrylic monomer (B), the (meth)acrylic monomer (C), and the (meth)acrylic monomer (D) is, with respect to the total amount of the (meth)acrylic monomer component, preferably 60% by mass or more, more preferably 80% by mass or more, and still more preferably 90% by mass or more.

<Photopolymerization Initiator>

The photocurable composition of the embodiment contains a photopolymerization initiator.

The photopolymerization initiator is not particularly limited as long as the initiator generates radicals by irradiation with light, and the photopolymerization initiator preferably generates radicals at the wavelength of light used for stereolithography.

Generally, the wavelength of light used for stereolithography is from 365 nm to 500 nm, and in practical use the wavelength is preferably from 365 nm to 430 nm, and more preferably from 365 nm to 420 nm.

Examples of a photopolymerization initiator which generates radicals at the wavelength of light used for stereolithography include an alkylphenone compound, an acylphosphine oxide compound, a titanocene compound, an oxime ester compound, a benzoin compound, an acetophenone compound, a benzophenone compound, a thioxanthone compound, an α-acyloxime ester compound, a phenyl glyoxylate compound, a benzyl compound, an azo compound, a diphenyl sulfide compound, an organic dye compound, an iron-phthalocyanine compound, a benzoin ether compound, and an anthraquinone compound.

Among these, from the viewpoint of reactivity, an alkyl phenone compound, or an acylphosphine oxide compound is preferable.

Example of an alkylphenone compound include 1-hydroxy-cyclohexyl-phenyl-ketone (IRGACURE 184: manufactured by BASF Corporation).

Examples of an acylphosphine oxide compound include bis(2,4,6-trimethylbenzoyl)-phenylphosphine oxide (IRGACURE 819: manufactured by BASF Corporation), and 2,4,6-trimethylbenzoyl-diphenyl-phosphine oxide (IRGACURE TPO: manufactured by BASF Corporation).

The photocurable composition of the present embodiment may contain only one photopolymerization initiator or two or more photopolymerization initiators.

The content (total content in the case of two or more kinds) of the photopolymerization initiator in the photocurable composition of the present embodiment is, with respect to 1000 parts by mass of the total content of (meth)acrylic monomer component, preferably from 1 part by mass to 50 parts by mass, more preferably from 2 parts by mass to 30 parts by mass, further preferably from 3 parts by mass to 25 parts by mass, and particularly preferably from 5 parts by mass to 20 parts by mass.

<Other Components>

The photocurable composition of the embodiment may contain, if necessary, at least one of other components other than the above.

The total content of the (meth)acrylic monomer component and the photopolymerization initiator is, with respect to the total amount of the photocurable composition, preferably 60% by mass or more, more preferably 80% by mass or more, and still more preferably 90% by mass or more.

Examples of other components include a coloring material.

For example, when the photocurable composition of the embodiment is used for manufacturing a denture base, from the viewpoint of aesthetics, the denture base may be colored to a color tone similar to gums by adding a coloring material to the photocurable composition.

The coloring material is not limited as long as the material does not interfere with molding with a 3D printer and it is difficult to discolor, and examples thereof include a pigment, a dye, and a coloring matter. More specifically, examples of the coloring material include a synthetic tar dye, an aluminum lake of a synthetic tar dye, an inorganic pigment, and a natural dye.

Examples of the other components include another curable resin (such as another curable monomer other than the above (meth)acrylic monomer component) other than the above (meth)acrylic monomer component.

Examples of the other components also include a thermal polymerization initiator.

When the photocurable composition of the embodiment contains a thermal polymerization initiator, both photocuring and thermal curing may be used in combination. Examples of the thermal polymerization initiator include a thermal radical generator and an amine compound.

Examples of the other components include an additive such as a coupling agent such as a silane coupling agent (for example, 3-acryloxypropyltrimethoxysilane), a rubber agent, an ion trapping agent, an ion exchanger, a leveling agent, a plasticizer, and an antifoaming agent.

The method of preparing the photocurable composition of the embodiment is not particularly limited, and examples thereof include a method of mixing an acrylic monomer (X), at least one of (meth)acrylic monomers (A) to (D), a photopolymerization initiator, and, if necessary, another component.

Means for mixing components is not particularly limited, and examples thereof includes ultrasonic melting, double arm stirrer, roll kneader, twin screw extruder, ball mill kneader, and planetary stirrer.

The photocurable composition of the embodiment may be prepared by mixing components, then filtering with a filter to remove impurities, and subjecting the filtered mixture to a vacuum defoaming treatment.

The glass transition temperature (Tg) of the photocurable composition of the embodiment after photocuring is not particularly limited, and from the viewpoint of flexural strength and flexural modulus, the glass transition temperature (Tg) after photocuring is preferably 70° C. or higher, and more preferably 80° C. or higher.

From the viewpoint of Charpy impact strength, the glass transition temperature (Tg) after photocuring is preferably 140° C. or lower.

[Denture Base, Plate Denture]

A denture base is particularly preferable as a dental prosthesis or the like which is a cured product (or, a stereolithography product) of the photocurable composition of the embodiment. The denture base which is a cured product of the photocurable composition of the embodiment is excellent in the flexural strength, flexural modulus, and Charpy impact strength.

The denture base according to the embodiment may be a denture base for a complete denture (so-called full denture) or a denture base for a partial denture (so-called partial).

The denture base of the embodiment may be a denture base for upper jaw denture (hereinafter also referred to as "upper jaw denture base"), a denture base for lower jaw denture (hereinafter also referred to as "lower jaw denture base"), or a set of an upper jaw denture base and a lower jaw denture base.

Only a part of the denture base of the embodiment may be manufactured using the photocurable composition of the embodiment or the whole may be manufactured using the photocurable composition of the embodiment.

Examples of the denture base only a part of which is manufactured using the photocurable composition of the embodiment include: a denture base (so-called metal base) including a metal portion and a resin portion in which at least a part of the resin portion is manufactured using the photocurable composition of the embodiment; and a denture base (so-called resin base) consisting only of a resin portion only a part of which is manufactured using the photocurable composition of the embodiment.

Example of the denture base manufactured entirely using the photocurable composition of the embodiment include a denture base composed of only a resin portion.

The plate denture of the embodiment includes the denture base of the embodiment and an artificial tooth fixed to the denture base.

The plate denture of the embodiment is excellent in the flexural strength, flexural modulus, and Charpy impact strength of the denture base.

The plate denture of the embodiment may be a partial denture or a complete denture. In other words, the plate denture of the embodiment may have at least one artificial tooth.

The plate denture of the embodiment may be an upper jaw denture, a lower jaw denture, or a set of an upper jaw denture and a lower jaw denture.

Examples of the material of an artificial tooth include an acrylic resin.

The artificial tooth may contain a filler or the like in addition to an acrylic resin.

EXAMPLES

Hereinafter, the invention will be specifically described by way of Examples, but the invention is not limited to these Examples.

Examples

Hereinafter, Examples (Examples 1 to 41) and Comparative Examples (Comparative Examples 1 to 16) are described.

Examples 1 to 41, Comparative Examples 1 to 16

<Preparation of Photocurable Composition>

The components shown in the following Tables 1 to 4 were mixed to obtain photocurable compositions. Since, in any Examples, no structures derived from bisphenol A were included in monomers used, the content of bisphenol A in the photocurable composition was 2.5 ppm or less.

When the content of bisphenol A is 2.5 ppm or less, the photocurable composition can also be advantageously used for public hygiene and dental materials.

<Measurements and Evaluations>

Using the obtained photocurable compositions, the following measurements and evaluations were carried out. The results are shown in Tables 1 to 4.

(Measurement of Viscosity of Photocurable Composition)

The viscosity of the photocurable composition was measured with an E type viscometer at 25° C. and at 50 rpm.

(Flexural Strength and Flexural Modulus of Stereolithography Product)

The obtained photocurable composition was shaped into a size of 64 mm×10 mm×3.3 mm in thickness using a 3D printer (MASTERPLUS S2011 manufactured by Carima Co., Ltd.) to obtain a shaped article. The obtained shaped article was irradiated with ultraviolet light having a wavelength of 365 nm under the condition of 5 J/cm$^2$, and was fully cured to obtain a stereolithography product.

The obtained stereolithography product (hereinafter referred to as "test piece") was stored in a thermostatic water bath at 37±1° C. for 50±12 hours.

The test piece was then taken out from the thermostatic water bath, and the flexural strength and flexural modulus of the taken test piece were each measured in accordance with ISO20795-1:2008. These measurements were carried out under the conditions of a tensile speed of 5±1 mm/min using a tensile compression test apparatus (manufactured by Intesco Co., Ltd.).

When the photocurable composition is used for manufacturing a dental prosthesis or the like (especially a denture base), the flexural strength is preferably 60 MPa or more, and more preferably 65 MPa or more.

In this case, the flexural modulus is preferably 1500 MPa or more, and more preferably 2000 MPa or more.

(Charpy Impact Strength)

The obtained photocurable composition was shaped into a size of 80 mm×10 mm×4 mm in thickness using a 3D printer (MASTERPLUS S2011 manufactured by Carima Co., Ltd.) to obtain a shaped article. The obtained shaped article was irradiated with ultraviolet light having a wavelength of 365 run under the condition of 5 J/cm$^2$, and was fully cured to obtain a stereolithography product.

The obtained stereolithography product (hereinafter referred to as "test piece") was stored in a thermostatic water bath at 37±1° C. for 50±2 hours.

The test piece was then taken out from the thermostatic water bath, and a notch of shape A having a depth of 2 mm was provided in the longitudinal center portion of the taken test piece to obtain a single notched test piece.

The Charpy impact strength of the obtained single-notched test piece was measured in accordance with ISO179-1:2010 (or JIS K 7111-1:2012). The Charpy impact strength was measured under conditions of a hammer capacity of 0.5 J, an idle swing angle of 148° C., a test temperature of 23° C., and edgewise impact.

When the photocurable composition is used for manufacturing a dental prosthesis or the like (especially a denture base), the Charpy impact strength is preferably 1.0 kJ/m$^2$ or more from the viewpoint of durability.

TABLE 1

| | | Type | Mw | The number of ether bonds in one molecule | Example 1 | Example 2 | Example 3 | Example 4 | Example 5 | Example 6 |
|---|---|---|---|---|---|---|---|---|---|---|
| Photocurable composition | Monomer (X) | HBPE-4 | 524.69 | 4 | 660 | 700 | 700 | | | |
| | | A-9300-1CL | 537.52 | 0 | | | | 600 | 580 | 600 |
| | | A-9300-2CL | 651.66 | 0 | | | | | | |
| | | A-9300-3CL | 765.8 | 0 | | | | | | |
| | | DCP-A | 304.38 | 0 | | | | | | |
| | | DCP-2EO-A | 392.49 | 2 | | | | | | |
| | | A-DOG | 326.38 | 0 | | | | | | |
| | | CD-406 | 252.31 | 0 | | | | | | |
| | | HBPE-2 | 436.59 | 2 | | | | | | |
| | Monomer (A) | FA-222A | 214.22 | 1 | 340 | | | 400 | | |
| | | 3PG | 328.4 | 2 | | | | | 420 | |
| | Monomer (B) | IB-XA | 208.3 | 0 | | 300 | | | | 400 |
| | | CHA | 154.21 | 0 | | | | | | |
| | Monomer (C) | EG | 198.22 | 0 | | | 300 | | | |
| | | 1.9ND-A | 268.35 | 0 | | | | | | |
| | Photopolymerization initiator | Ir819 | — | — | 10 | 10 | 10 | 10 | 10 | 10 |
| | | Ir184 | — | — | | | | | | |
| | | TPO | — | — | | | | | | |
| Evaluation | | Viscosity (mPa · s) | | | 85 | 95 | 90 | 120 | 130 | 160 |
| | | Flexural strength (MPa) | | | 68 | 66 | 71 | 74 | 72 | 73 |
| | | Flexural modulus (MPa) | | | 2120 | 2135 | 2160 | 2360 | 2260 | 2460 |
| | | Charpy impact value (kJ/m$^2$) | | | 1.1 | 1.2 | 1.1 | 1.1 | 1.1 | 1.2 |

| | | Type | Mw | The number of ether bonds in one molecule | Example 7 | Example 8 | Example 9 | Example 10 | Example 11 | Example 12 |
|---|---|---|---|---|---|---|---|---|---|---|
| Photocurable composition | Monomer (X) | HBPE-4 | 524.69 | 4 | | | | | | |
| | | A-9300-1CL | 537.52 | 0 | 720 | 800 | 750 | 590 | 690 | 690 |
| | | A-9300-2CL | 651.66 | 0 | | | | | | |
| | | A-9300-3CL | 765.8 | 0 | | | | | | |
| | | DCP-A | 304.38 | 0 | | | | | | |
| | | DCP-2EO-A | 392.49 | 2 | | | | | | |
| | | A-DOG | 326.38 | 0 | | | | | | |
| | | CD-406 | 252.31 | 0 | | | | | | |
| | | HBPE-2 | 436.59 | 2 | | | | | | |
| | Monomer (A) | FA-222A | 214.22 | 1 | | | | | | |
| | | 3PG | 328.4 | 2 | | | | 200 | 200 | |
| | Monomer (B) | IB-XA | 208.3 | 0 | | | | 210 | | 200 |
| | | CHA | 154.21 | 0 | 280 | | | | | |
| | Monomer (C) | EG | 198.22 | 0 | | 200 | | | 110 | 110 |
| | | 1.9ND-A | 268.35 | 0 | | | 250 | | | |
| | Photopolymerization initiator | Ir819 | — | — | 10 | 10 | 10 | 10 | 10 | 10 |
| | | Ir184 | — | — | | | | | | |
| | | TPO | — | — | | | | | | |
| Evaluation | | Viscosity (mPa · s) | | | 145 | 180 | 240 | 140 | 160 | 170 |
| | | Flexural strength (MPa) | | | 67 | 74 | 65 | 73 | 73 | 73 |
| | | Flexural modulus (MPa) | | | 2260 | 2350 | 2015 | 2380 | 2310 | 2430 |
| | | Charpy impact value (kJ/m$^2$) | | | 1.1 | 1.1 | 1.1 | 1.2 | 1.1 | 1.1 |

TABLE 1-continued

|  | Type | Mw | The number of ether bonds in one molecule | Example 13 | Example 14 | Example 15 | Example 16 | Example 17 | Example 18 |
|---|---|---|---|---|---|---|---|---|---|
| Photocurable composition | Monomer (X) | HBPE-4 | 524.69 | 4 | | | | | | |
| | | A-9300-1CL | 537.52 | 0 | | | | | | |
| | | A-9300-2CL | 651.66 | 0 | 700 | 650 | 650 | | | |
| | | A-9300-3CL | 765.8 | 0 | | | | 650 | 600 | 600 |
| | | DCP-A | 304.38 | 0 | | | | | | |
| | | DCP-2EO-A | 392.49 | 2 | | | | | | |
| | | A-DOG | 326.38 | 0 | | | | | | |
| | | CD-406 | 252.31 | 0 | | | | | | |
| | | HBPE-2 | 436.59 | 2 | | | | | | |
| | Monomer (A) | FA-222A | 214.22 | 1 | 300 | | | 350 | | |
| | | 3PG | 328.4 | 2 | | | | | | |
| | Monomer (B) | IB-XA | 208.3 | 0 | | 350 | | | 400 | |
| | | CHA | 154.21 | 0 | | | | | | |
| | Monomer (C) | EG | 198.22 | 0 | | | 350 | | | 400 |
| | | 1.9ND-A | 268.35 | 0 | | | | | | |
| | Photopolymerization initiator | Ir819 | — | — | 10 | 10 | 10 | 10 | 10 | 10 |
| | | Ir184 | — | — | | | | | | |
| | | TPO | — | — | | | | | | |
| Evaluation | | Viscosity (mPa·s) | | | 155 | 120 | 110 | 110 | 100 | 95 |
| | | Flexural strength (MPa) | | | 69 | 68 | 69 | 68 | 67 | 68 |
| | | Flexural modulus (MPa) | | | 2160 | 2245 | 2280 | 2045 | 2090 | 2105 |
| | | Charpy impact value (kJ/m$^2$) | | | 1.2 | 1.2 | 1.2 | 1.3 | 1.3 | 1.2 |

TABLE 2

|  | Type | Mw | The number of ether bonds in one molecule | Example 19 | Example 20 | Example 21 | Example 22 | Example 23 | Example 24 |
|---|---|---|---|---|---|---|---|---|---|
| Monomer (X) | HBPE-4 | 524.69 | 4 | | | | | | |
| | A-9300-1CL | 537.52 | 0 | | | | | | |
| | A-9300-2CL | 651.66 | 0 | | | | | | |
| | A-9300-3CL | 765.8 | 0 | | | | | | |
| | DCP-A | 304.38 | 0 | 800 | 800 | 800 | | | |
| | DCP-2EO-A | 392.49 | 2 | | | | 600 | 600 | 600 |
| | A-DOG | 326.38 | 0 | | | | | | |
| | CD-406 | 252.31 | 0 | | | | | | |
| | HBPE-2 | 436.59 | 2 | | | | | | |
| Monomer (A) | FA-222A | 214.22 | 1 | | | | 400 | | |
| | 3PG | 328.4 | 2 | 200 | | | | | |
| Monomer (B) | IB-XA | 208.3 | 0 | | | | | 400 | |
| | CHA | 154.21 | 0 | | 200 | | | | |
| Monomer (C) | EG | 198.22 | 0 | | | | | | 400 |
| | 1.9ND-A | 268.35 | 0 | | | 200 | | | |
| Photopolymerization initiator | Ir819 | — | — | 10 | 10 | 10 | 10 | 10 | 10 |
| | Ir184 | — | — | | | | | | |
| | TPO | — | — | | | | | | |
| | Viscosity (mPa·s) | | | 60 | 65 | 70 | 80 | 85 | 80 |
| | Flexural strength (MPa) | | | 72 | 71 | 68 | 69 | 71 | 72 |
| | Flexural modulus (MPa) | | | 2430 | 2420 | 2090 | 2160 | 2130 | 2180 |
| | Charpy impact value (kJ/m$^2$) | | | 1.1 | 1.1 | 1.2 | 1.3 | 1.3 | 1.2 |

|  | Type | Mw | The number of ether bonds in one molecule | Example 25 | Example 26 | Example 27 | Example 28 | Example 29 | Example 30 |
|---|---|---|---|---|---|---|---|---|---|
| Monomer (X) | HBPE-4 | 524.69 | 4 | | | | | | |
| | A-9300-1CL | 537.52 | 0 | | | | | | |
| | A-9300-2CL | 651.66 | 0 | | | | | | |
| | A-9300-3CL | 765.8 | 0 | | | | | | |
| | DCP-A | 304.38 | 0 | | | | | | |
| | DCP-2EO-A | 392.49 | 2 | | | | | | |
| | A-DOG | 326.38 | 0 | 700 | 700 | 700 | | | |
| | CD-406 | 252.31 | 0 | | | | 700 | 700 | 700 |
| | HBPE-2 | 436.59 | 2 | | | | | | |
| Monomer (A) | FA-222A | 214.22 | 1 | | | | | | |
| | 3PG | 328.4 | 2 | 300 | | | 300 | | |
| Monomer (B) | IB-XA | 208.3 | 0 | | | | | | |
| | CHA | 154.21 | 0 | | 300 | | | 300 | |
| Monomer (C) | EG | 198.22 | 0 | | | | | | |
| | 1.9ND-A | 268.35 | 0 | | | 300 | | | 300 |

TABLE 2-continued

| | Type | | | | | | | | |
|---|---|---|---|---|---|---|---|---|---|
| Photopolymerization initiator | Ir819 | | | 10 | 10 | 10 | 10 | 10 | 10 |
| | Ir184 | — | — | | | | | | |
| | TPO | — | — | | | | | | |
| | Viscosity (mPa·s) | | | 110 | 115 | 105 | 50 | 55 | 65 |
| | Flexural strength (MPa) | | | 78 | 75 | 72 | 71 | 73 | 68 |
| | Flexural modulus (MPa) | | | 2510 | 2470 | 2245 | 2235 | 2360 | 2185 |
| | Charpy impact value (kJ/m$^2$) | | | 1.1 | 1.1 | 1.1 | 1.1 | 1.1 | 1.1 |

| | Type | Mw | The number of ether bonds in one molecule | Example 31 | Example 32 | Example 33 | Example 34 | Example 35 | Example 36 |
|---|---|---|---|---|---|---|---|---|---|
| Monomer (X) | HBPE-4 | 524.69 | 4 | | | | | | |
| | A-9300-1CL | 537.52 | 0 | | | | | 600 | 580 | 600 |
| | A-9300-2CL | 651.66 | 0 | | | | | | | |
| | A-9300-3CL | 765.8 | 0 | | | | | | | |
| | DCP-A | 304.38 | 0 | | | | | | | |
| | DCP-2EO-A | 392.49 | 2 | | | | | | | |
| | A-DOG | 326.38 | 0 | | | | | | | |
| | CD-406 | 252.31 | 0 | | | | | | | |
| | HBPE-2 | 436.59 | 2 | 700 | 700 | 700 | | | |
| Monomer (A) | FA-222A | 214.22 | 1 | 300 | | | 400 | | |
| | 3PG | 328.4 | 2 | | | | | 420 | |
| Monomer (B) | IB-XA | 208.3 | 0 | | 300 | | | | 400 |
| | CHA | 154.21 | 0 | | | | | | |
| Monomer (C) | EG | 198.22 | 0 | | | 300 | | | |
| | 1.9ND-A | 268.35 | 0 | | | | | | |
| Photopolymerization initiator | Ir819 | — | — | 10 | 10 | 10 | | | |
| | Ir184 | — | — | | | | 10 | 10 | 10 |
| | TPO | — | — | | | | 10 | 10 | 10 |
| | Viscosity (mPa·s) | | | 135 | 150 | 140 | 130 | 140 | 170 |
| | Flexural strength (MPa) | | | 71 | 74 | 73 | 75 | 73 | 74 |
| | Flexural modulus (MPa) | | | 2330 | 2450 | 2470 | 2380 | 2280 | 2470 |
| | Charpy impact value (kJ/m$^2$) | | | 1.2 | 1.2 | 1.2 | 1.1 | 1.1 | 1.2 |

TABLE 3

| | | Type | Mw | The number of ether bonds in one molecule | Example 37 | Example 38 | Example 39 | Example 40 | Example 41 |
|---|---|---|---|---|---|---|---|---|---|
| Photocurable composition | Monomer (X) | HBPE-4 | 524.69 | 4 | 600 | | | | |
| | | A-9300-1CL | 537.52 | 0 | | | | 550 | 300 |
| | | A-9300-2CL | 651.66 | 0 | | | | | |
| | | A-9300-3CL | 765.8 | 0 | | | | | |
| | | DCP-A | 304.38 | 0 | | 450 | 300 | | |
| | | DCP-2EO-A | 392.49 | 2 | | | | | |
| | | A-DOG | 326.38 | 0 | | | | | |
| | | CD-406 | 252.31 | 0 | | | | | |
| | | HBPE-2 | 436.59 | 2 | | | | | |
| | Monomer (A) | FA-222A | 214.22 | 1 | | | | | |
| | | 3PG | 328.4 | 2 | | | | | |
| | Monomer (B) | IB-XA | 208.3 | 0 | | | | | |
| | | CHA | 154.21 | 0 | | | | | |
| | Monomer (C) | EG | 198.22 | 0 | | | | | |
| | | 1.9ND-A | 268.35 | 0 | | | | | |
| | Monomer (D) | POB-A | 254.28 | 1 | | 550 | | 450 | |
| | | A-LEN10 | 268.31 | 1 | 400 | | 700 | | 700 |
| | Photopolymerization initiator | Ir819 | — | — | 10 | 10 | 10 | 10 | 10 |
| | | Ir184 | — | — | | | | | |
| | | TPO | — | — | | | | | |
| Evaluation | | Viscosity | | | 280 | 40 | 130 | 220 | 360 |
| | | Flexural strength | | | 68 | 75 | 93 | 75 | 77 |
| | | Flexural modulus | | | 2050 | 2890 | 3300 | 2350 | 2900 |
| | | Charpy impact value | | | 1.3 | 1.2 | 1.1 | 1.4 | 1.3 |

TABLE 4

| | | Type | Mw | The number of ether bonds in one molecule | Comparative Example 1 | Comparative Example 2 | Comparative Example 3 | Comparative Example 4 | Comparative Example 5 | Comparative Example 6 |
|---|---|---|---|---|---|---|---|---|---|---|
| Photocurable composition | Monomer (X) | HBPE-4 | 524.69 | 4 | 600 | | | | | |
| | | A-9300-1CL | 537.52 | 0 | | | 700 | 700 | 700 | |
| | | DCP-A | 304.38 | 0 | | | | | | |

TABLE 4-continued

| | | Type | Mw | The number of ether bonds in one molecule | | | | | | |
|---|---|---|---|---|---|---|---|---|---|---|
| | Monomer (A) | FA-222A | 214.22 | 1 | | | | | | |
| | | 3PG | 328.4 | 2 | | | | | 300 | |
| | Monomer (B) | IB-XA | 208.3 | 0 | | | | | | 300 |
| | | CHA | 154.21 | 0 | | | | | | |
| | Monomer (C) | EG | 198.22 | 0 | | | | | | |
| | | 1.9ND-A | 268.35 | 0 | | | | | | |
| | Other monomers | HBPEM-10 | 817.04 | 10 | | | | | 700 | 700 |
| | | DCP | 322.43 | 0 | | | | | | |
| | | A-TMPT | 296.32 | 0 | | | | | | |
| | | FA-240A | 522.57 | 8 | 400 | 300 | | | | |
| | | LA | 240.38 | 0 | | | 300 | | | |
| | | 1.12DDDA | 310.43 | 0 | | | | 300 | | |
| | | M-113 | 450.62 | 4 | | | | | | |
| | Photopolymerization initiator | Ir819 | — | — | 10 | 10 | 10 | 10 | 10 | 10 |
| | | Ir184 | — | — | | | | | | |
| | | TPO | — | — | | | | | | |
| Evaluation | | Viscosity (mPa·s) | | | 120 | 270 | 220 | 100 | 75 | 70 |
| | | Flexural strength (MPa) | | | 25 | 33 | 22 | 31 | 73 | 78 |
| | | Flexural modulus (MPa) | | | 400 | 700 | 360 | 670 | 2550 | 2580 |
| | | Charpy impact value (kJ/m²) | | | 2.2 | 1.9 | 2.2 | 1.9 | 0.5 | 0.5 |

| | | Type | Mw | The number of ether bonds in one molecule | Comparative Example 7 | Comparative Example 8 | Comparative Example 9 | Comparative Example 10 | Comparative Example 11 |
|---|---|---|---|---|---|---|---|---|---|
| Photocurable composition | Monomer (X) | HBPE-4 | 524.69 | 4 | | | | | |
| | | A-9300-1CL | 537.52 | 0 | | | | | |
| | | DCP-A | 304.38 | 0 | | | | | |
| | Monomer (A) | FA-222A | 214.22 | 1 | | 300 | | | |
| | | 3PG | 328.4 | 2 | | | | | |
| | Monomer (B) | IB-XA | 208.3 | 0 | | | 300 | | |
| | | CHA | 154.21 | 0 | | | | | |
| | Monomer (C) | EG | 198.22 | 0 | | | | 300 | |
| | | 1.9ND-A | 268.35 | 0 | 300 | | | | |
| | Other monomers | HBPEM-10 | 817.04 | 10 | | 700 | 700 | 700 | |
| | | DCP | 322.43 | 0 | 700 | | | | |
| | | A-TMPT | 296.32 | 0 | | | | | 1000 |
| | | FA-240A | 522.57 | 8 | | | | | |
| | | LA | 240.38 | 0 | | | | | |
| | | 1.12DDDA | 310.43 | 0 | | | | | |
| | | M-113 | 450.62 | 4 | | | | | |
| | Photopolymerization initiator | Ir819 | — | — | 10 | 10 | 10 | 10 | 10 |
| | | Ir184 | — | — | | | | | |
| | | TPO | — | — | | | | | |
| Evaluation | | Viscosity (mPa·s) | | | 75 | 120 | 110 | 110 | 100 |
| | | Flexural strength (MPa) | | | 79 | 45 | 50 | 53 | 66 |
| | | Flexural modulus (MPa) | | | 2600 | 870 | 1400 | 1480 | 2300 |
| | | Charpy impact value (kJ/m²) | | | 0.5 | 1.8 | 1.5 | 1.5 | 0.6 |

| | | Type | Mw | The number of ether bonds in one molecule | Comparative Example 12 | Comparative Example 13 | Comparative Example 14 | Comparative Example 15 | Comparative Example 16 |
|---|---|---|---|---|---|---|---|---|---|
| Photocurable composition | Monomer (X) | HBPE-4 | 524.69 | 4 | | | | | |
| | | A-9300-1CL | 537.52 | 0 | | | | | |
| | | DCP-A | 304.38 | 0 | | | | 1000 | 400 |
| | Monomer (A) | FA-222A | 214.22 | 1 | | | | | |
| | | 3PG | 328.4 | 2 | 400 | | | | |
| | Monomer (B) | IB-XA | 208.3 | 0 | | | | | |
| | | CHA | 154.21 | 0 | | 300 | | | |
| | Monomer (C) | EG | 198.22 | 0 | | | | | |
| | | 1.9ND-A | 268.35 | 0 | | | 300 | | |
| | Other monomers | HBPEM-10 | 817.04 | 10 | | | | | |
| | | DCP | 322.43 | 0 | | | | | |
| | | A-TMPT | 296.32 | 0 | 600 | 700 | 700 | | |
| | | FA-240A | 522.57 | 8 | | | | | |
| | | LA | 240.38 | 0 | | | | | |
| | | 1.12DDDA | 310.43 | 0 | | | | | |
| | | M-113 | 450.62 | 4 | | | | | 600 |
| | Photopolymerization initiator | Ir819 | — | — | 10 | 10 | 10 | 10 | |
| | | Ir184 | — | — | | | | | |
| | | TPO | — | — | | | | | |

TABLE 4-continued

| Evaluation | Viscosity (mPa · s) | 50 | 40 | 40 | 120 | 110 |
|---|---|---|---|---|---|---|
| | Flexural strength (MPa) | 72 | 69 | 67 | 77 | 18 |
| | Flexural modulus (MPa) | 2340 | 2250 | 2060 | 2580 | 280 |
| | Charpy impact value (kJ/m$^2$) | 0.6 | 0.6 | 0.6 | 0.6 | 2.1 |

Description of Tables 1 to 4

In Tables 1 to 4,
the amount (number) of each component in each Example and each Comparative Example is based on "part by mass",
"Monomer (X)" represents an acrylic monomer (X),
"Monomer (A)" represents a (meth)acrylic monomer (A),
"Monomer (B)" represents a (meth)acrylic monomer (B),
"Monomer (C)" represents a (meth)acrylic monomer (C),
"Monomer (D)" represents a (meth)acrylic monomer (D), and
"Other monomer" represents other (meth)acrylic monomers other than the acrylic monomer (X) and the (meth)acrylic monomers (A) to (D).

In Tables 1 to 4, the structure of each of the acrylic monomers (X) is as follows.

Here, HBPE-2 and HBPE-4 are acrylic monomers manufactured by DKS Co. Ltd., A-9300-1CL, A-9300-2CL, A-9300-3CL, and A-DOG are acrylic monomers manufactured by Shin-Nakamura Chemical Co., Ltd., DCP-A and DCP-2EO-A are acrylic monomers manufactured by Kyoeisha Chemical Co., Ltd., and CD406 is an acrylic monomer manufactured by Sartomer Company.

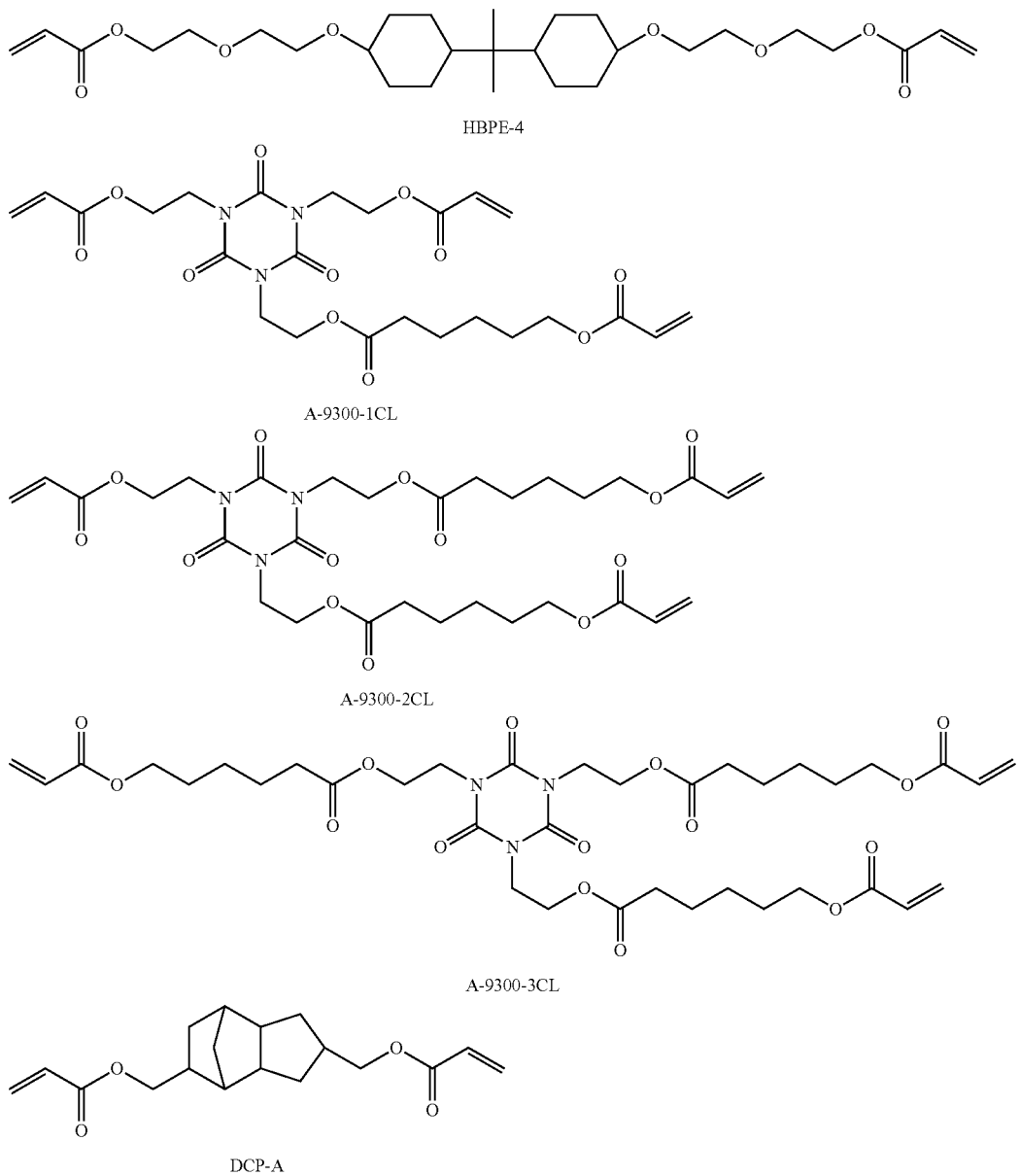

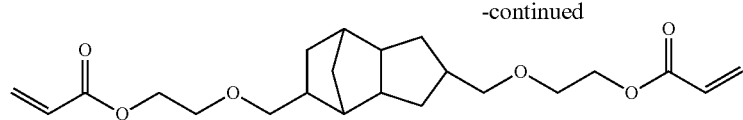

DCP-2EO-A

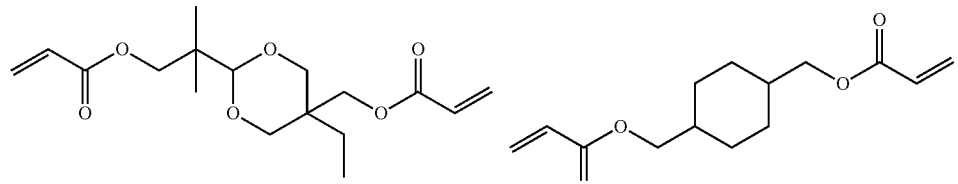

A-DOG

A-DOG

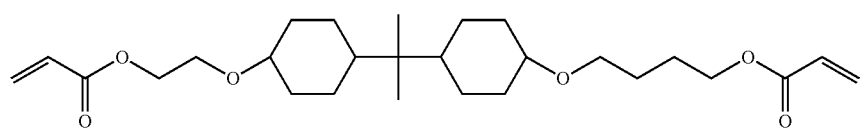

HBPE-2

In Tables 1 to 4, the structure of each of the (meth)acrylic monomers (A) is as follows.

Here, FA-222A is an acrylic monomer manufactured by Hitachi Chemical Co., Ltd., and 3PG is a methacrylic monomer manufactured by Shin-Nakamura Chemical Co., Ltd.

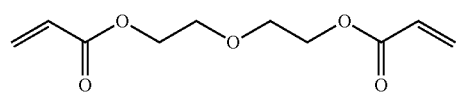

FA-222A

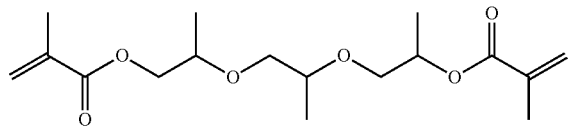

3PG

In Tables 1 to 4, the structure of each of the (meth)acrylic monomers (B) is as follows.

Here, IB-XA is an acrylic monomer manufactured by Kyoeisha Chemical Co., Ltd., and CHA is an acrylic monomer manufactured by Osaka Organic Chemical Industry Ltd.

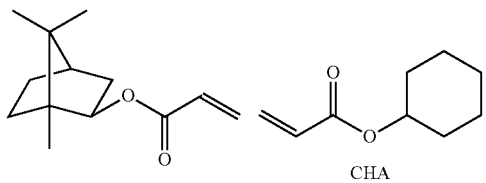

IB-XA    CHA

In Tables 1 to 4, the structure of each of the (meth)acrylic monomers (C) is as follows.

Here, EG is a methacrylic monomer manufactured by Kyoeisha Chemical Co., Ltd., and 1,9ND-A is an acrylic monomer manufactured by Kyoeisha Chemical Co., Ltd.

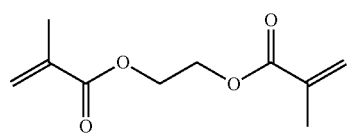

EG

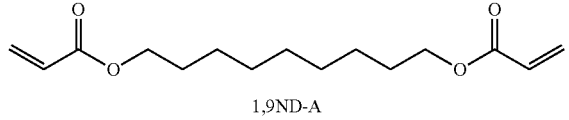

1,9ND-A

In Table 3, the structure of each of the (meth)acrylic monomers (D) is as follows.

Here, POB-A is an acrylic monomer manufactured by Kyoeisha Chemical Co., Ltd., and A-LEN-10 is an acrylic monomer manufactured by Shin-Nakamura Chemical Co., Ltd.

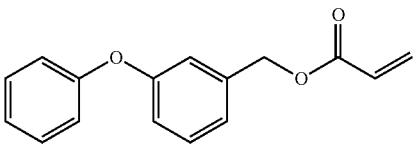

POB-A

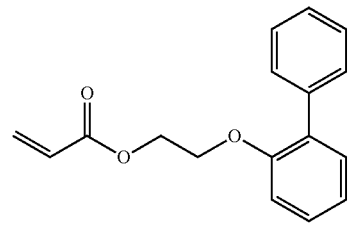

A-LEN-10

In Table 4, the structures of other monomers are as follows.

Here, HBPEM-10 is a methacrylic monomer manufactured by DKS Co. Ltd., DCP is a methacrylic monomer manufactured by Kyoeisha Chemical Co., Ltd., A-TMPT is an acrylic monomer manufactured by Shin-Nakamura Chemical Co., Ltd., FA-240A is an acrylic monomer manufactured by Hitachi Chemical Co., Ltd., LA is an acrylic monomer manufactured by Osaka Organic Chemical Industry Ltd., 1,12DDDA is 1,12-dodecanediol diacrylate, and M-113 is an acrylic monomer manufactured by TOAGOSEI CO., LTD.

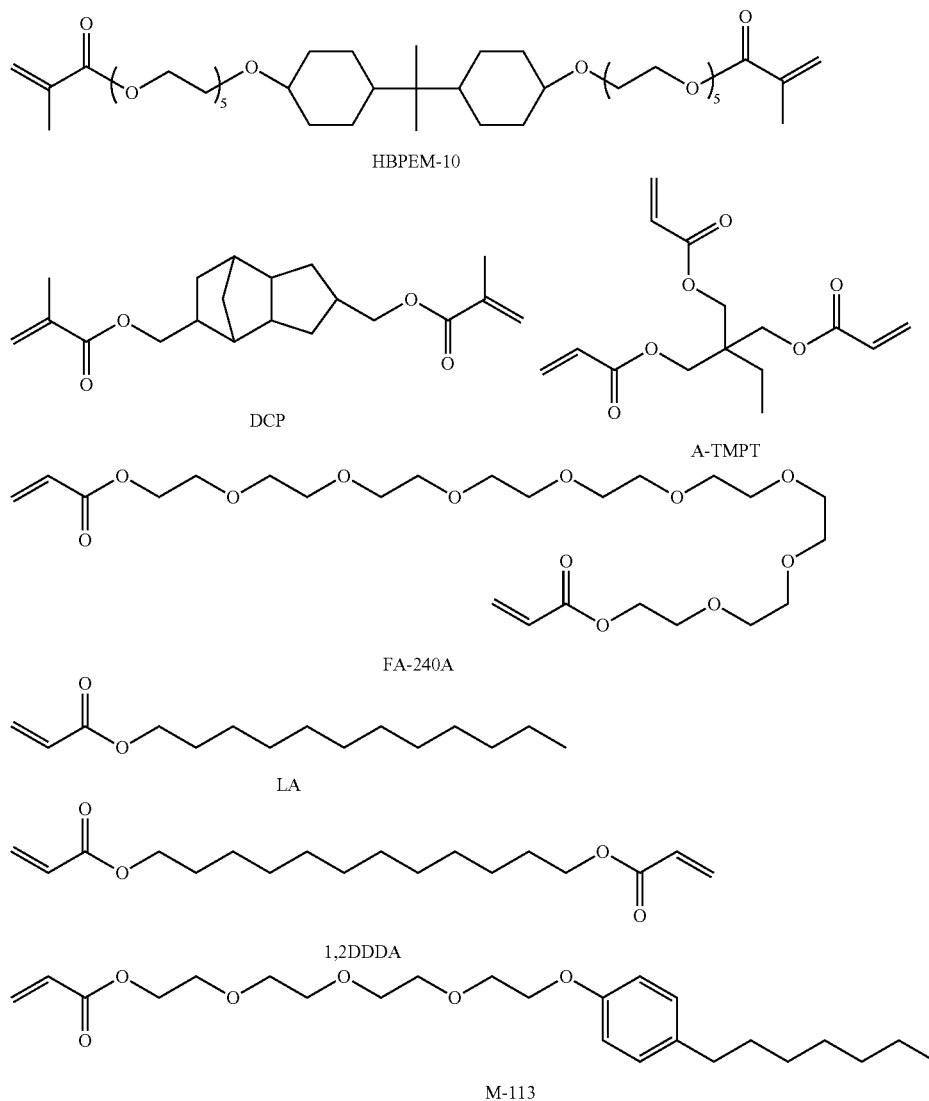

Among the photopolymerization initiators in Tables 1 to 4, Irg819 is "IRGACURE 819" (acylphosphine oxide compound) manufactured by BASF Corporation, Irg184 is "IRGACURE 184" (alkylphenone compound) manufactured by BASF Corporation, and TPO is "IRGACURE TPO" (acylphosphine oxide compound) manufactured by BASF Corporation. The structure of each of these photopolymerization initiators is as follows.

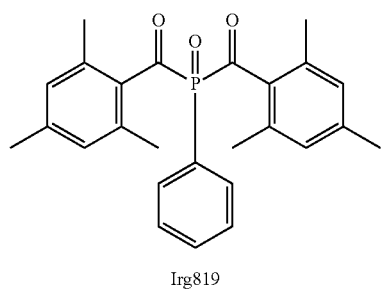

As shown in Tables 1 to 3, in Examples 1 to 41 using a photocurable composition containing the acrylic monomer (X) described above, at least one selected from the group consisting of the (meth)acrylic monomer (A), the (meth)acrylic monomer (B), the (meth)acrylic monomer (C), and the (meth)acrylic monomer (D) described above, and a photopolymerization initiator, it was possible to obtain a stereolithography product satisfying all the requirements of flexural strength of 60 MPa or more, flexural modulus of 1500 MPa or more, and Charpy impact strength of 1.0 kJ/m² or more. The viscosities of the photocurable compositions of Examples 1 to 41 were viscosities suitable for stereolithography.

As described above, it was confirmed that the photocurable compositions of Examples 1 to 41 were particularly suitable for manufacturing a dental prosthesis or the like (especially denture base) by stereolithography.

In contrast to Examples 1 to 41, in Comparative Examples 1 to 4 and Comparative Examples 16 in which another monomer (FA-240A, LA, 1,12DDDA, or M-113) was used in place of the (meth)acrylic monomers (A) to (D), the flexural strength and flexural modulus of the stereolithography product were insufficient.

In Comparative Examples 5 to 7 in which another monomer (DCP) was used in place of the acrylic monomer (X), the Charpy impact strength of the stereolithography product was insufficient.

In Comparative Examples 8 to 10 in which another monomer (HBPEM-10) was used in place of the acrylic monomer (X), the flexural strength and flexural modulus of the stereolithography product were insufficient.

In Comparative Example 11 using only another monomer without using the acrylic monomer (X) and the (meth)acrylic monomer (A) to (C), and Comparative Examples 12 to 14 using another monomer (A-TMPT) in place of the acrylic monomer (X), the Charpy impact strength of the stereolithography product was insufficient.

In Comparative Example 15 using only the acrylic monomer (X), the Charpy impact strength of the stereolithography product was insufficient.

The entire disclosure of Japanese Patent Application No. 2016-152160 filed on Aug. 2, 2016 is incorporated herein by reference.

All documents, patent applications, and technical standards described in this specification are herein incorporated by reference to the same extent as if each individual document, patent application, or technical standard was specifically and individually indicated to be incorporated by reference.

The invention claimed is:

1. A photocurable composition which is used for manufacturing a dental prosthesis, a medical instrument used intraorally, or a tooth jaw model by stereolithography,
the photocurable composition containing a (meth)acrylic monomer component and a photopolymerization initiator,
wherein the (meth)acrylic monomer component comprises:
an acrylic monomer (X), which is at least one selected from acrylic monomers having no aromatic rings and having a ring structure other than an aromatic ring and two or more acryloyloxy groups in one molecule, and which has a weight average molecular weight of from 200 to 800, and
at least one selected from the group consisting of: a (meth)acrylic monomer (A) which is at least one selected from di(meth)acrylic monomers having no aromatic rings and having one or more ether bonds and two (meth)acryloyloxy groups in one molecule, and which has a weight average molecular weight of from 200 to 400; a (meth)acrylic monomer (B), which is at least one selected from (meth)acrylic monomers having no aromatic rings and having a ring structure other than an aromatic ring and one (meth)acryloyloxy group in one molecule, and which has a weight average molecular weight of from 130 to 240; a (meth)acrylic monomer (C) which is at least one selected from di(meth)acrylic monomers having no aromatic rings and no ether bonds and having a hydrocarbon skeleton and two (meth)acryloyloxy groups in one molecule, and which has a weight average molecular weight of from 190 to 280; and a (meth)acrylic monomer (D) which is at least one selected from (meth)acrylic monomers having one or more aromatic rings and one (meth)acryloyloxy group in one molecule, and which has a weight average molecular weight of from 140 to 350, and
in the (meth)acrylic monomer component, a total content of the acrylic monomer (X), the (meth)acrylic monomer (A), the (meth)acrylic monomer (B), the (meth)acrylic monomer (C), and the (meth)acrylic monomer (D) is 80% by mass or more with respect to a total amount of the (meth)acrylic monomer component,
in a case in which the photocurable composition comprises the (meth)acrylic monomer (A) and neither comprises the (meth)acrylic monomer (B), the (meth)acrylic monomer (C), nor the (meth)acrylic monomer (D), at least one acrylic monomer constituting the acrylic monomer (X) is dimethylol-tricyclodecane diacrylate, ethoxylated dimethylol-tricyclodecane diacrylate (EO=2 mol), or an acrylic monomer having two or more acryloyloxy groups and one or more ring structures selected from the group consisting of a cyclohexane skeleton not including a tetrahydrodicyclopentadienyl skeleton, and a heterocyclic ring structure in which a number of atoms constituting the ring is from 5 to 20,
in a case in which the photocurable composition comprises the (meth)acrylic monomer (D), a content of the (meth)acrylic monomer (D), with respect to 1000 parts by mass of a total content of the (meth)acrylic monomer component, is from 300 parts by mass to 750 parts by mass, and
in a case in which the photocurable composition comprises the (meth)acrylic monomer (C), a content of the (meth)acrylic monomer (C), with respect to 1000 parts by mass of a total content of the (meth)acrylic monomer component, is from 100 parts by mass to 350 parts by mass.

2. The photocurable composition according to claim 1, wherein
the (meth)acrylic monomer component comprises:
the acrylic monomer (X); and
at least one selected from the group consisting of the (meth)acrylic monomer (A), the (meth)acrylic monomer (B), and the (meth)acrylic monomer (C).

3. The photocurable composition according to claim 1, wherein
in a case in which the photocurable composition comprises at least one selected from the group consisting of the (meth)acrylic monomer (B), the (meth)acrylic monomer (C), and the (meth)acrylic monomer (D), at least one acrylic monomer constituting the acrylic monomer (X) is an acrylic monomer having one or more ring structures selected from the group consisting of an alicyclic ring structure having from 5 to 20 carbon atoms and a heterocyclic ring structure in which a number of atoms constituting the ring is from 5 to 20, and two or more acryloyloxy groups.

4. The photocurable composition according to claim 1, wherein
in a case in which the photocurable composition comprises at least one selected from the group consisting of the (meth)acrylic monomer (B), the (meth)acrylic monomer (C), and the (meth)acrylic monomer (D), at least one acrylic monomer constituting the acrylic monomer (X) is an acrylic monomer having one or more ring structures selected from the group consisting of a tetrahydrodicyclopentadienyl skeleton, a cyclohexane skeleton, an isocyanur skeleton, and a 1,3-dioxane skeleton, and two or more acryloyloxy groups.

5. The photocurable composition according to claim 1, wherein
at least one di(meth)acrylic monomer constituting the (meth)acrylic monomer (A) is a compound represented by the following Formula (a-1):

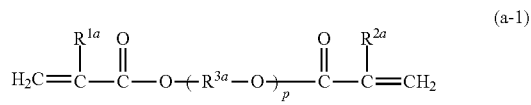

wherein, in Formula (a-1), each of $R^{1a}$ and $R^{2a}$ independently represents a hydrogen atom or a methyl group, $R^{3a}$ represents a linear or branched alkylene group having from 2 to 4 carbon atoms, and p represents from 2 to 4.

6. The photocurable composition according to claim 1, wherein
at least one di(meth)acrylic monomer constituting the (meth)acrylic monomer (A) is a compound represented by the following Formula (a-2):

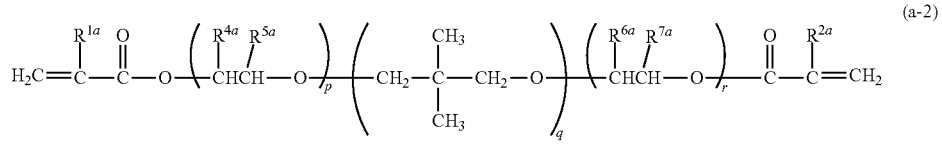

wherein, in Formula (a-2), each of $R^{1a}$, $R^{2a}$, $R^{4a}$, $R^{5a}$, $R^{6a}$, and $R^{7a}$ independently represents a hydrogen atom or a methyl group, each of p, q, and r independently represents 0 or 1, and $p+q+r \geq 2$ is satisfied.

7. The photocurable composition according to claim 1, wherein
at least one (meth)acrylic monomer constituting the (meth)acrylic monomer (B) is a compound represented by the following Formula (b-1):

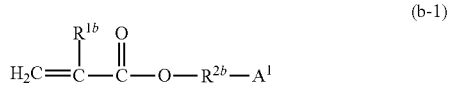

wherein, in Formula (b-1), $R^{1b}$ represents a hydrogen atom or a methyl group, $R^{2b}$ represents a single bond or a methylene group, and $A^1$ represents a ring structure other than an aromatic ring.

8. The photocurable composition according to claim 1, wherein
at least one (meth)acrylic monomer constituting the (meth)acrylic monomer (B) is a compound represented by the following Formula (b-2):

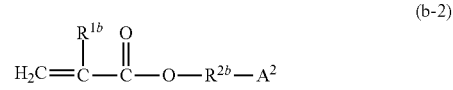

wherein, in Formula (b-2), $R^{1b}$ represents a hydrogen atom or a methyl group, $R^{2b}$ represents a single bond or a methylene group, and $A^2$ represents a ring structure having a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton.

9. The photocurable composition according to claim 1, wherein
at least one di(meth)acrylic monomer constituting the (meth)acrylic monomer (C) is a compound represented by the following Formula (c-1):

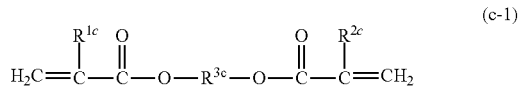

wherein, in Formula (c-1), each of $R^{1c}$ and $R^{2c}$ independently represents a hydrogen atom or a methyl group, and $R^{3c}$ represents an alkylene group having from 1 to 9 carbon atoms.

10. The photocurable composition according to claim 1, wherein
at least one di(meth)acrylic monomer constituting the (meth)acrylic monomer (C) is a compound represented by the following Formula (c-1):

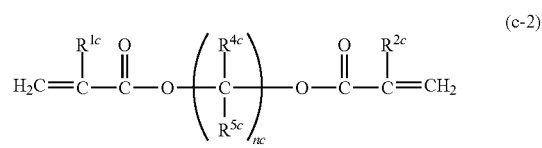

wherein, in Formula (c-2), each of $R^{1c}$ and $R^{2c}$ independently represents a hydrogen atom or a methyl group, each of $R^{4c}$ and $R^{5c}$ independently represents a hydrogen atom or a methyl group, nc represents from 1 to 9, and the alkylene group represented by $-(CR^{4c}R^{5c})_{nc}-$ has from 1 to 9 carbon atoms.

11. The photocurable composition according to claim 1, wherein
at least one of (meth)acrylic monomers constituting the (meth)acrylic monomer (D) is a compound represented by the following Formula (d-1):

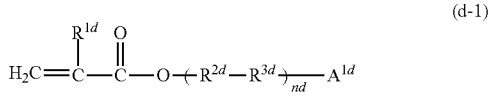

(d-1)

wherein, in Formula (d-1), $R^{1d}$ represents a hydrogen atom or a methyl group, $R^{2d}$ represents a single bond or a linear or branched alkylene group having from 1 to 5 carbon atoms, $R^{3d}$ represents a single bond, an ether bond (—O—), an ester bond (—O—(C=O)—), or —$C_6H_4$—O—, $A^{1d}$ represents an aromatic ring which may have a substituent, and nd represents from 1 to 2.

12. The photocurable composition according to claim 1, wherein
the photopolymerization initiator is at least one selected from the group consisting of an alkyl phenone compound and an acylphosphine oxide compound.

13. The photocurable composition according to claim 1, wherein
a content of the acrylic monomer (X), with respect to 1000 parts by mass of a total content of the (meth)acrylic monomer component, is from 550 parts by mass to 850 parts by mass.

14. The photocurable composition according to claim 13, wherein
a content of the (meth)acrylic monomer (A), with respect to 1000 parts by mass of a total content of the (meth)acrylic monomer component, is from 180 parts by mass to 450 parts by mass.

15. The photocurable composition according to claim 1, wherein
a content of the (meth)acrylic monomer (B), with respect to 1000 parts by mass of a total content of the (meth)acrylic monomer component, is from 100 parts by mass to 450 parts by mass.

16. The photocurable composition according to claim 1, wherein
a content of the photopolymerization initiator, with respect to 1000 parts by mass of a total content of the (meth)acrylic monomer component, is from 1 part by mass to 50 parts by mass.

17. The photocurable composition according to claim 1, wherein
a viscosity measured using an E type viscometer at 25° C. and at 50 rpm is from 20 mPa·s to 1500 mPa·s.

18. The photocurable composition according to claim 1, wherein
a content of bisphenol A is 2.5 ppm or less.

19. A denture base which is a cured product of the photocurable composition according to claim 1.

20. A plate denture comprising: the denture base according to claim 19; and an artificial tooth fixed to the denture base.

21. A photocurable composition which is used for manufacturing a dental prosthesis, a medical instrument used intraorally, or a tooth jaw model by stereolithography,
the photocurable composition containing a (meth)acrylic monomer component and a photopolymerization initiator,
wherein the (meth)acrylic monomer component comprises:
an acrylic monomer (X), which is at least one selected from acrylic monomers having no aromatic rings and having a ring structure other than an aromatic ring and two or more acryloyloxy groups in one molecule, and which has a weight average molecular weight of from 200 to 800, and
at least one selected from the group consisting of: a (meth)acrylic monomer (A) which is at least one selected from di(meth)acrylic monomers having no aromatic rings and having one or more ether bonds and two (meth)acryloyloxy groups in one molecule, and which has a weight average molecular weight of from 200 to 400; a (meth)acrylic monomer (B), which is at least one selected from (meth)acrylic monomers having no aromatic rings and having a ring structure other than an aromatic ring and one (meth)acryloyloxy group in one molecule, and which has a weight average molecular weight of from 130 to 240; a (meth)acrylic monomer (C) which is at least one selected from di(meth)acrylic monomers having no aromatic rings and no ether bonds and having a hydrocarbon skeleton and two (meth)acryloyloxy groups in one molecule, and which has a weight average molecular weight of from 190 to 280; and a (meth)acrylic monomer (D) which is at least one selected from (meth)acrylic monomers having one or more aromatic rings and one (meth)acryloyloxy group in one molecule, and which has a weight average molecular weight of from 140 to 300, and
in the (meth)acrylic monomer component, a total content of the acrylic monomer (X), the (meth)acrylic monomer (A), the (meth)acrylic monomer (B), the (meth)acrylic monomer (C), and the (meth)acrylic monomer (D) is 80% by mass or more with respect to a total amount of the (meth)acrylic monomer component,
in a case in which the photocurable composition comprises the (meth)acrylic monomer (A) and neither comprises the (meth)acrylic monomer (B), the (meth)acrylic monomer (C), nor the (meth)acrylic monomer (D), at least one acrylic monomer constituting the acrylic monomer (X) is ethoxylated dimethylol-tricyclodecane diacrylate (EO=2 mol), or an acrylic monomer having two or more acryloyloxy groups and one or more ring structures selected from the group consisting of a cyclohexane skeleton not including a tetrahydrodicyclopentadienyl skeleton, and a heterocyclic ring structure in which a number of atoms constituting the ring is from 5 to 20, and
in a case in which the photocurable composition comprises the (meth)acrylic monomer (C), a content of the (meth)acrylic monomer (C), with respect to 1000 parts by mass of a total content of the (meth)acrylic monomer component, is from 100 parts by mass to 350 parts by mass.

22. A method of manufacturing a dental prosthesis, a medical instrument used intraorally, or a tooth jaw model by stereolithography, comprising:
shaping a photocurable composition into a shape of the dental prosthesis, the medical instrument used intraorally, or the tooth jaw model, and
photocuring the obtained shaped article,
the photocurable composition containing a (meth)acrylic monomer component and a photopolymerization initiator,
wherein the (meth)acrylic monomer component comprises:
an acrylic monomer (X), which is at least one selected from acrylic monomers having no aromatic rings and having a ring structure other than an aromatic ring and two or more acryloyloxy groups in one molecule, and which has a weight average molecular weight of from 200 to 800, and at least one selected from the group consisting of: a (meth)acrylic monomer (A) which is at least one selected from di(meth)acrylic monomers having no aromatic rings and having one or more ether bonds and two (meth)acryloyloxy groups in one molecule, and which has a weight average molecular weight of from 200 to 400; a (meth)acrylic monomer (B), which is at least one selected from (meth)acrylic monomers having no aromatic rings and having a ring structure other than an aromatic ring and one (meth)acryloyloxy group in one molecule, and which has a weight average molecular weight of from 130 to 240; a (meth)acrylic monomer (C) which is at least one selected from di(meth)acrylic monomers having no aromatic rings and no ether bonds and having a hydrocarbon skeleton and two (meth)acryloyloxy groups in one molecule, and which has a weight average molecular weight of from 190 to 280; and a (meth)acrylic monomer (D) which is at least one selected from (meth)acrylic monomers having one or more aromatic rings and one (meth)acryloyloxy group in one molecule, and which has a weight average molecular weight of from 140 to 350, and in the (meth)acrylic monomer component, a total content of the acrylic monomer (X), the (meth)acrylic monomer (A), the (meth)acrylic monomer (B), the (meth)acrylic monomer (C), and the (meth)acrylic monomer (D) is 80% by mass or more with respect to a total amount of the (meth)acrylic monomer component, in a case in which the photocurable composition comprises the (meth)acrylic monomer (A) and neither comprises the (meth)acrylic monomer (B), the (meth)acrylic monomer (C), nor the (meth)acrylic monomer (D), at least one acrylic monomer constituting the acrylic monomer (X) is dimethylol-tricyclodecane diacrylate, ethoxylated dimethylol-tricyclodecane diacrylate (EO=2 mol), or an acrylic monomer having two or more acryloyloxy groups and one or more ring structures selected from the group consisting of a cyclohexane skeleton not including a tetrahydrodicyclopentadienyl skeleton, and a heterocyclic ring structure in which a number of atoms constituting the ring is from 5 to 20.

* * * * *